(12) United States Patent
Murayama et al.

(10) Patent No.: US 8,654,184 B2
(45) Date of Patent: Feb. 18, 2014

(54) ELECTRIC ENDOSCOPE AND ENDOSCOPE SYSTEM

(75) Inventors: Masahiko Murayama, Hachioji (JP); Kunihiko Hijihara, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/584,508

(22) Filed: Aug. 13, 2012

(65) Prior Publication Data
US 2013/0050457 A1 Feb. 28, 2013

Related U.S. Application Data

(63) Continuation of application No. PCT/JP2012/055572, filed on Mar. 5, 2012.

(30) Foreign Application Priority Data

Mar. 15, 2011 (JP) ................................. 2011-057051

(51) Int. Cl.
*H04N 7/18* (2006.01)
(52) U.S. Cl.
USPC .................... 348/65; 348/72; 348/75; 348/76
(58) Field of Classification Search
USPC ..................................................... 375/65–76
See application file for complete search history.

(56) References Cited

U.S. PATENT DOCUMENTS

| | | | |
|---|---|---|---|
| 4,519,391 A | 5/1985 | Murakoshi | |
| 4,895,138 A | 1/1990 | Yabe | |
| 4,989,586 A | 2/1991 | Furukawa | |
| 5,868,664 A * | 2/1999 | Speier et al. | ................... 600/112 |
| 2007/0106119 A1 | 5/2007 | Hirata et al. | |
| 2009/0076329 A1 | 3/2009 | Su et al. | |

FOREIGN PATENT DOCUMENTS

| | | |
|---|---|---|
| GB | 2148661 A | 5/1985 |
| GB | 2 148 661 A | 11/1987 |
| JP | A-2001-128936 | 5/2001 |
| JP | A-2001-221957 | 8/2001 |
| JP | A-2007-89888 | 4/2007 |
| JP | 4343890 B2 | 10/2009 |

OTHER PUBLICATIONS

Apr. 10, 2012 International Search Report issued in International Application No. PCT/JP2012/055572 (with translation).

(Continued)

*Primary Examiner* — Andy Rao
(74) *Attorney, Agent, or Firm* — Oliff PLC

(57) ABSTRACT

An electronic endoscope includes an insertion portion including an insulative distal end hard portion main body at a distal end thereof, an operation portion provided at a proximal end portion of the insertion portion and including a connector connection electrically connected to a ground portion, a ground metal member provided between the main body and the operation portion, forming a structure of the insertion portion, and being electrically conductive to the ground portion through the connector connection, an observation optical system including an optical element and a frame member having conductive properties and holding the optical element, and being extended from the distal end of the insertion portion toward the operation portion, and a conductive connecting portion allowing the frame member of the observation optical system to become electrically conductive with respect to the ground metal member.

5 Claims, 17 Drawing Sheets

(56) References Cited

OTHER PUBLICATIONS

Mar. 13, 2013 Extended European Search Report issued in European Patent Application No. 12757546.2.

Jul. 30, 2013 Office Action issued in Chinese Patent Application No. 201280001760.3 (with English Translation).

Oct. 22, 2013 Search Report issued in European Patent Application No. 12 757 546.2-1660.

* cited by examiner

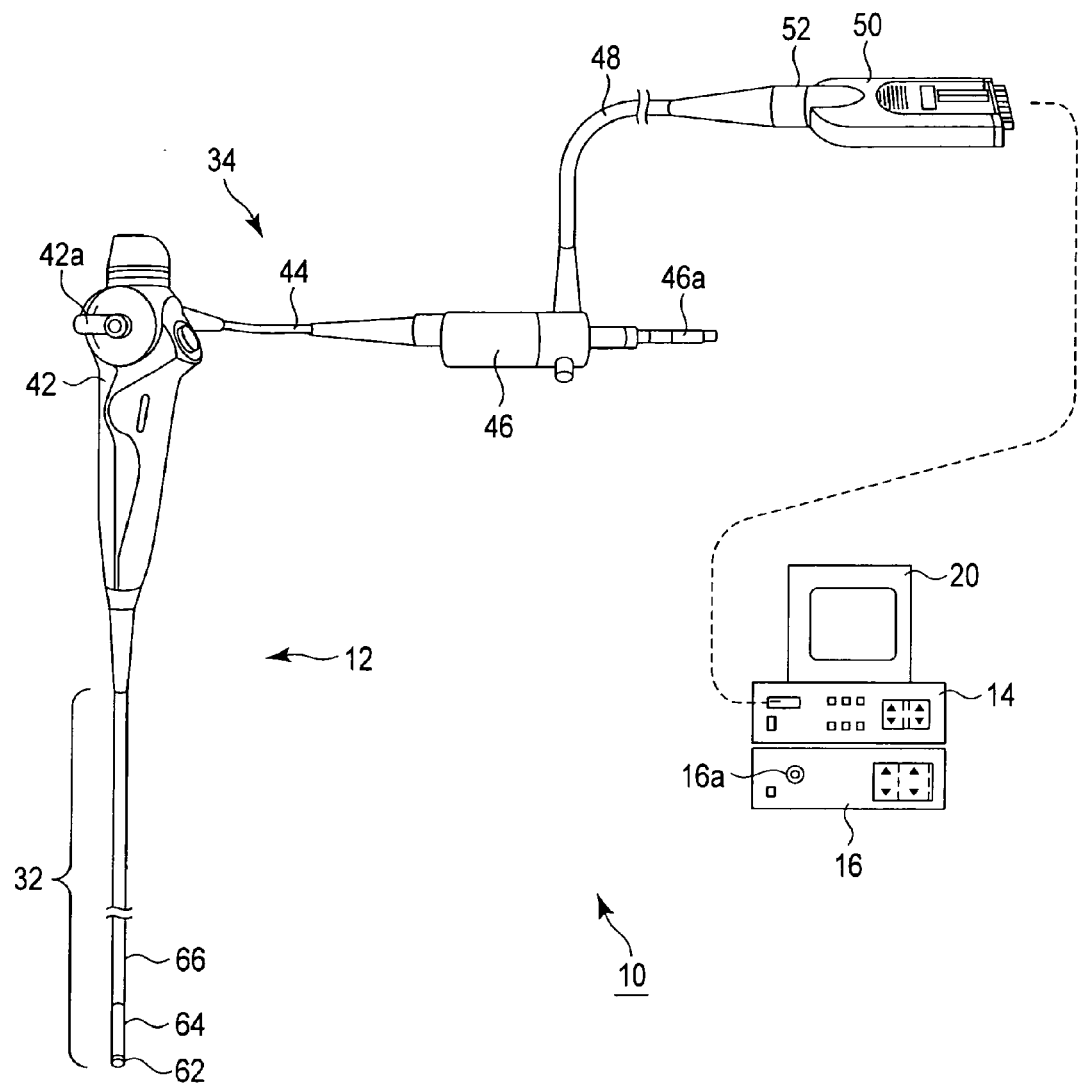
F I G. 1

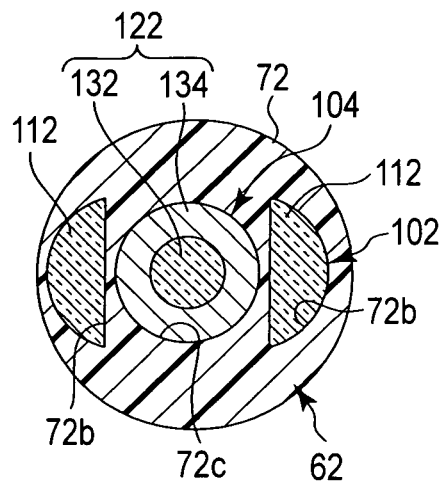
F I G. 2B
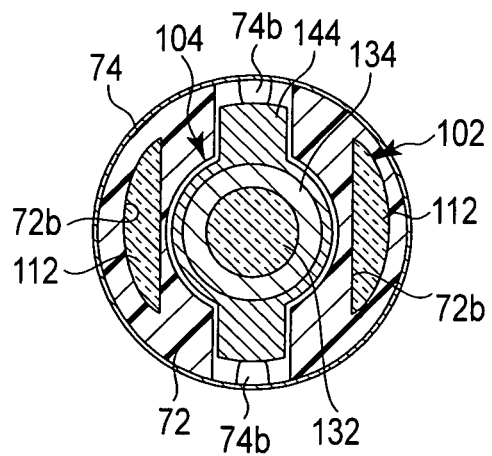
F I G. 2C

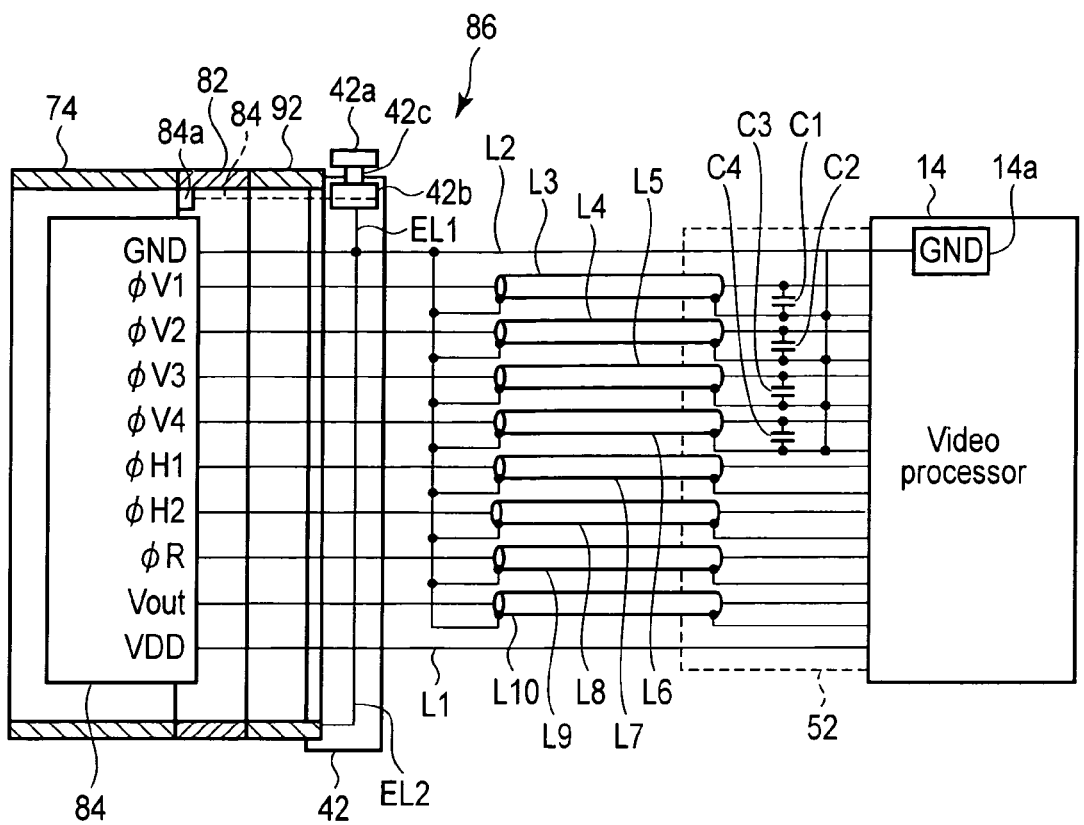
F I G. 3A

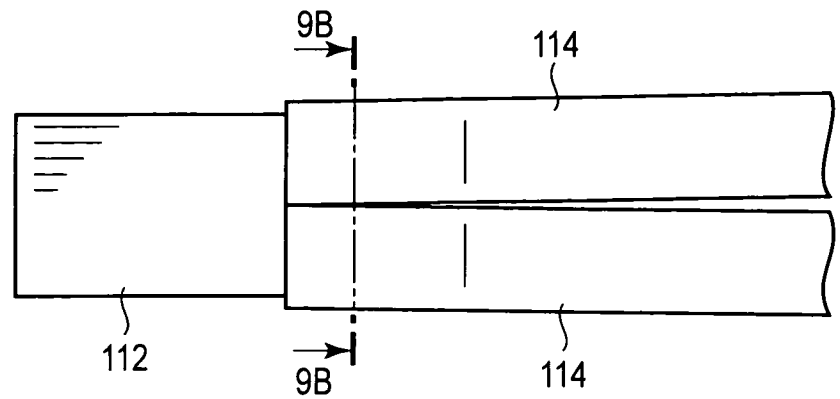
F I G. 9A
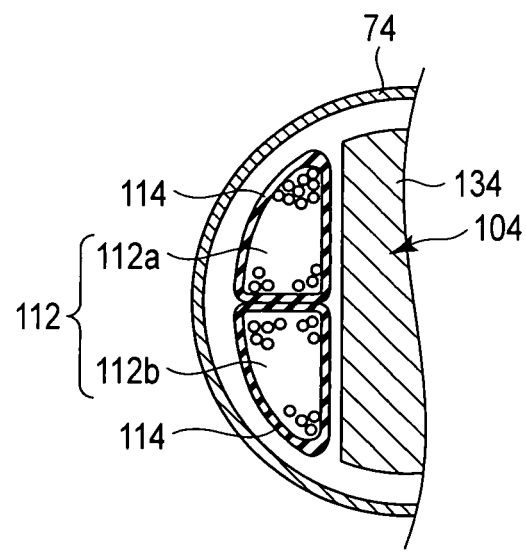
F I G. 9B

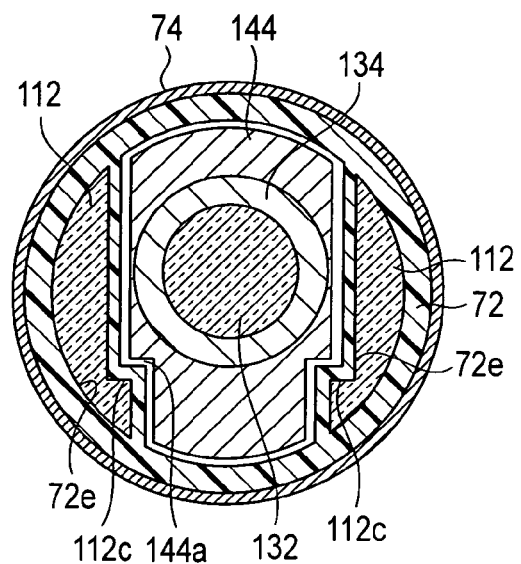
F I G. 10A
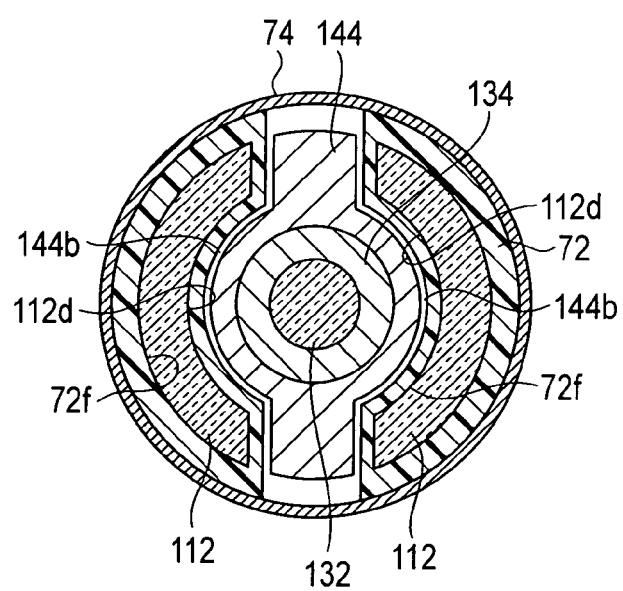
F I G. 10B

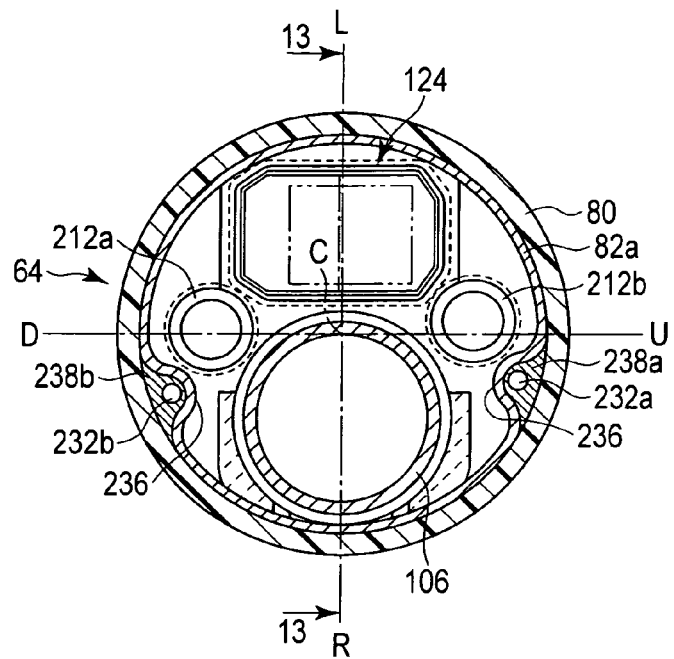
F I G. 14A
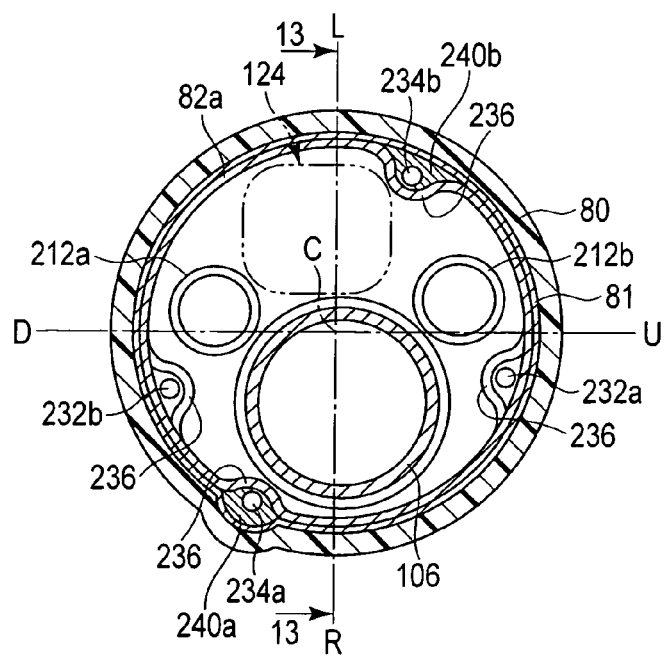
F I G. 14B

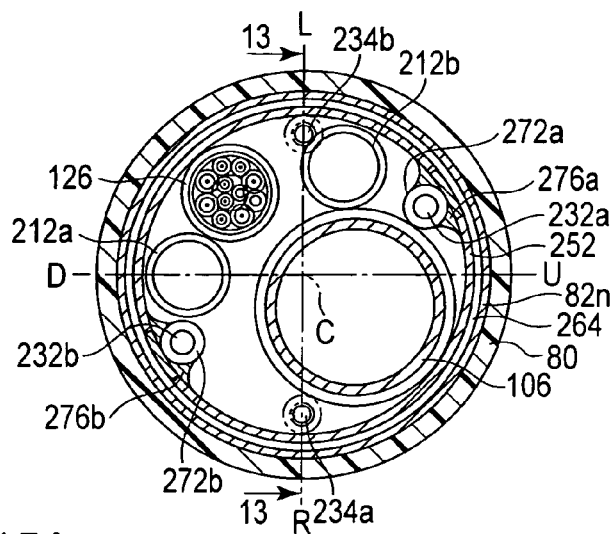
F I G. 15A
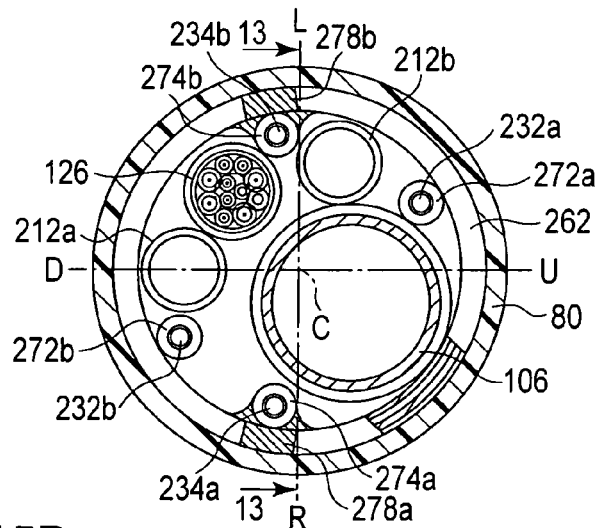
F I G. 15B
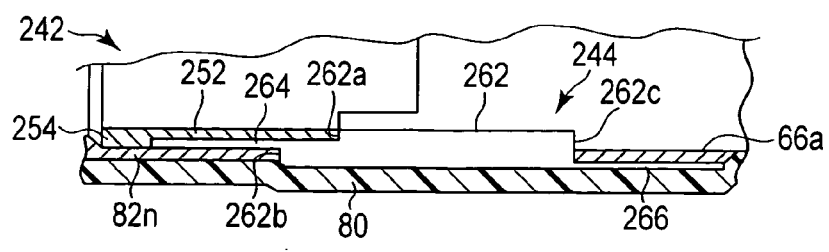
F I G. 15C

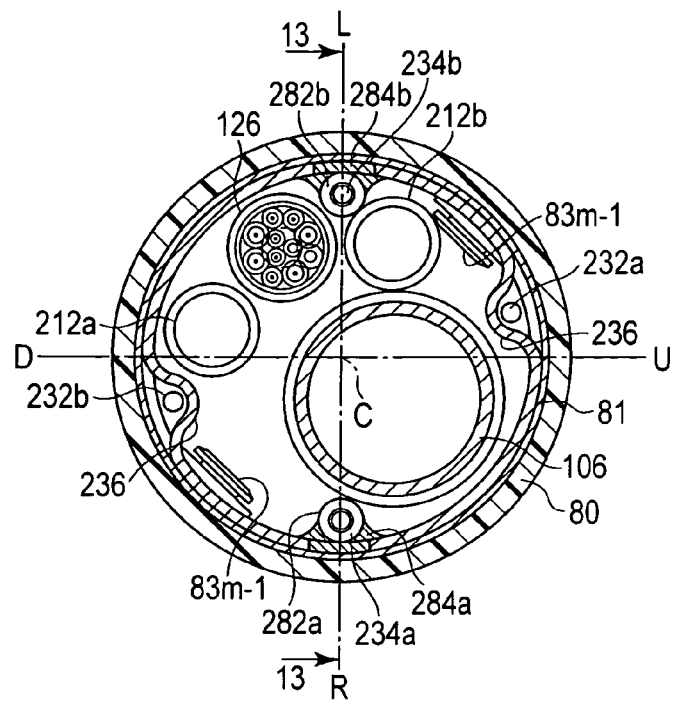
F I G. 16A
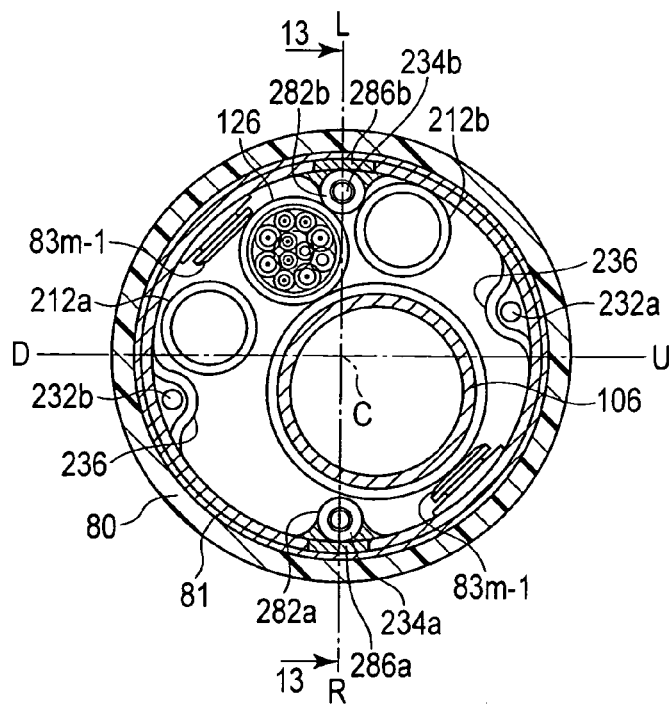
F I G. 16B

ELECTRIC ENDOSCOPE AND ENDOSCOPE SYSTEM

CROSS-REFERENCE TO RELATED APPLICATIONS

This is a Continuation application of PCT Application No. PCT/JP2012/055572, filed Mar. 5, 2012, which was published under PCT Article 21(2) in Japanese.

This application is based upon and claims the benefit of priority from the prior Japanese Patent Application No. 2011-057051, filed Mar. 15, 2011, the entire contents of which are incorporated herein by reference.

BACKGROUND OF THE INVENTION

1. Field of the Invention

This invention relates to an electronic endoscope and an endoscopic system which are used for various purposes such as industrial or medical purposes.

2. Description of the Related Art

In general, an observation optical system is arranged in an insertion portion of an electronic endoscope and, in particular, an objective lens and a solid-state image sensing device (a CCD) connected with an imaging cable extended toward a proximal end side of the inserting portion are arranged in a distal end portion of the insertion portion. In practice, the objective lens is held in an objective lens frame, the solid-state image sensing device is held in a CCD holding frame, and these members are arranged in the distal end portion of the insertion portion of the endoscope with the CCD holding frame being assembled to a rear end of the objective lens frame. In regard to the endoscope, an image formed on the solid-state image sensing device through the objective lens is acquired by the solid-state image sensing device, the image is converted into an electrical signal, and the electrical signal is output to a video processor which is provided outside the endoscope through the imaging cable, thereby displaying a video picture in a monitor.

In recent years, for example, a high-frequency treatment device is combined with an electronic endoscope and used in some cases. In such a situation, a leak current from the high-frequency treatment device may flow through a solid-state image sensing device from a distal end portion of an insertion portion of the endoscope, and an observation image obtained by the endoscope may be affected by noise. Furthermore, when static electricity is produced during use of the endoscope, a current obtained by the static electricity may flow through the solid-state image sensing device from the distal end portion of the endoscope.

For example, a distal end portion main body of an insertion portion of an endoscope disclosed in Jpn. Pat. Appln. KOKAI Publication No. 2001-128936 is generally formed of a conductive metal member, and the distal end main body is contact with a metal structure member constituting an exterior and an inner structure of the endoscope. For example, static electricity or a leak current from a high-frequency treatment device is electrically connected to the metal structure member by allowing the current to flow through the metal structure member of the endoscope via the distal end portion main body. When the current is let to flow through a ground portion of a video processor outside the endoscope, the current is prevented from flowing through a solid-state image sensing device.

Further, in recent years, there is an endoscope in which a distal end portion main body of an insertion portion is made of a transparent insulating material (a non-conductive material). This configuration is adopted because of a reduction in price cost attained by integrating an illumination lens provided to the distal end portion main body with the distal end portion main body or a reduction in diameter of the distal end portion main body. In case of the endoscope, since the distal end portion main body is made of the non-conductive material, the distal end portion main body of the insertion portion of the endoscope cannot be electrically connected to the metal structure member as different from Jpn. Pat. Appln. KOKAI Publication No. 2001-128936. Therefore, static electricity or a high-frequency leak current flows through a metal objective lens frame exposed from the distal end portion main body, and the current may possibly flow through the solid-state image sensing device via a CCD holding frame.

To solve such problems, Jpn. Pat. Appln. KOKAI Publication No. 2007-89888 discloses a technology for electrically connecting a CCD reinforced frame, to which a rear end of a CCD holding frame is fitted and which covers an imaging substrate to assure strength of a solid-state image sensing device or the imaging substrate, with a GND of an imaging cable by using a conducive wire arranged in an insertion portion. Based on the countermeasure, a current that has flowed in an objective lens frame to flow through the CCD holding frame does not flow through the solid-state image sensing device but flows to the GND of a video processor via the CCD reinforcing frame, the conductive wire, and the GND of the imaging cable. Therefore, in the endoscope disclosed in Jpn. Pat. Appln. KOKAI Publication No. 2007-89888, an influence of static electricity or a high-frequency leak current on the solid-state image sensing device is avoided. In the endoscope disclosed in Jpn. Pat. Appln. KOKAI Publication No. 2007-89888, to enhance conductive properties between the objective lens frame, the CCD holding frame, and the CCD reinforce frame, the objective lens frame is bonded to the CCD holding frame and the CCD holding frame is bonded to the CCD reinforced frame by using a conductive adhesive.

BRIEF SUMMARY OF THE INVENTION

An electronic endoscope includes: an insertion portion which includes an insulative distal end hard portion main body at a distal end thereof and which is configured to be inserted into a hole; an operation portion which is provided at a proximal end portion of the insertion portion and which includes a connector connecting portion electrically connected to a ground portion; a ground metal member which is provided between the distal end hard portion main body of the insertion portion and the operation portion, which forms a structure of the insertion portion, and which is electrically conductive with respect to the ground portion through the connector connecting portion; an observation optical system which includes an optical element and a frame member having conductive properties and holding the optical element, and which is extended from the distal end of the insertion portion toward the operation portion; and a conductive connecting portion which allows the frame member of the observation optical system to become electrically conductive with respect to the ground metal member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing an entire endoscopic system according to a first embodiment;

FIG. 2B is a schematic transverse cross-sectional view taken along a line 2B-2B in FIG. 2A;

FIG. 2C is a schematic transverse cross-sectional view taken along a line 2C-2C in FIG. 2A;

FIG. 3A is a schematic view showing an electrically connected state of a solid-state image sensing device and a video processor in the endoscopic system according to the first embodiment;

FIG. 9A is a schematic view showing the light guide for use in the endoscope in the endoscopic system according to each of the first to fourth embodiments;

FIG. 9B is a schematic transverse cross-sectional view showing a state that an observation optical system and the light guide are aligned in a connection tube along a line 9B-9B in FIG. 9A;

FIG. 10A is a schematic transverse cross-sectional view showing a state that the observation optical system and the light guide are aligned in the connection tube;

FIG. 10B is a schematic transverse cross-sectional view showing a state that the observation optical system and the light guide are aligned in the connection tube;

FIG. 14A is a schematic transverse cross-sectional view of the endoscope according to the reference embodiment taken along a line 14A-14A in FIG. 13;

FIG. 14B is a schematic transverse cross-sectional view of the endoscope according to the reference conformation taken along a line 14B-14B in FIG. 13;

FIG. 15A is a schematic transverse cross-sectional view of the endoscope according to the reference embodiment taken along a line 15A-15A in FIG. 13;

FIG. 15B is a schematic transverse cross-sectional view of the endoscope according to the reference embodiment taken along a line 15B-15B in FIG. 13;

FIG. 15C is a schematic enlarged view of the endoscope according to the reference conformation at a position designated by reference sign 15C;

FIG. 16A is a schematic transverse cross-sectional view of the endoscope according to the reference embodiment taken along a line 16A-16A in FIG. 13; and FIG. 16B is a schematic transverse cross-sectional view of the endoscope according to the reference conformation taken along a line 16B-16B in FIG. 13.

DETAILED DESCRIPTION OF THE INVENTION

Figure 2A:
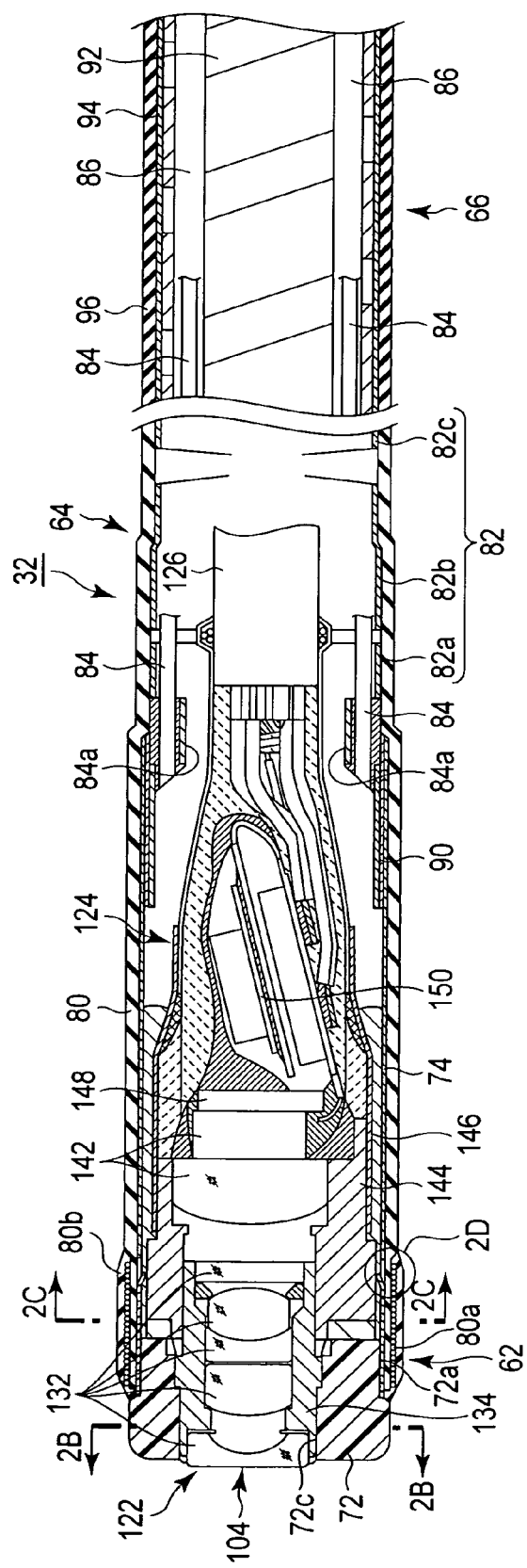
FIG. 2A is a schematic longitudinal cross-sectional view of an insertion portion of an endoscope in the endoscopic system according to the first embodiment.

Modes for carrying out the present invention will now be described hereinafter with reference to the drawings.

A first embodiment will be explained with reference to FIG. 1 to FIG. 3B.

As shown in FIG. 1, an endoscopic system 10 according to the embodiment includes an electronic endoscope 12, and a video processor 14 and a light source apparatus 16 which can be attached to or detached from the electronic endoscope 12. The video processor 14 and the light source apparatus 16 are external devices with respect to the electronic endoscope 12, respectively. A monitor 20 is connected to the video processor 14.

The electronic endoscope 12 includes an elongated insertion portion 32 configured to be inserted into a narrow space such as a lumen and an operation portion 34 which is provided at a proximal end portion of the insertion portion 32 and configured to operate the insertion portion 32.

The operation portion 34 has an operation portion main body 42 having a bending operation knob (a bending operating portion) 42a, a universal cord 44, a light guide connector 46, a video cable 48, and an electrical connector (a connector connecting portion) 50.

The inside of the operation portion main body 42 accommodates various structures extended from the inside of the insertion portion 32 and functions as an accommodating portion which accommodates a rotation portion 42b such as a pulley or a sprocket configured to bend a later-described bending portion 64, and the outside of the operation portion main body 42 functions as a grip portion which is gripped by a user. The bending operation knob 42a interlocks with the rotation portion 42b in the operation portion main body 42 through a shaft portion 42c. Therefore, when the bending operation knob 42a is operated, a later-described wire 84 is operated through the rotation portion 42b, and a bending tube 82, i.e., the bending portion 64 can be bent. It is to be noted that the rotation portion 42b is preferably made of a metal material and has conductive properties. On the other hand, at least outer peripheries of the operation portion main body 42 and the bending operation knob 42a are covered with a resin material or the like having insulation properties.

The universal cord 44 is extended from the operation portion main body 42. The universal cord 44 is covered with an insulating resin material, e.g., polyurethane. A light guide connector 46 having a light guide end portion 46a connected to a concave portion 16a of the light source apparatus 16 is arranged at a distal end portion of the universal cord 44 with respect to the operation portion main body 42. A video cable 48 is extended from a side surface of the light guide connector 46, and an electrical connector 50 connected to the video processor 14 is arranged at a distal end portion of the video cable 48 with respect to the light guide connector 46.

The insertion portion 32 shown in FIG. 1 and FIG. 2A includes a distal end hard portion 62, a bending portion 64, and a tubular portion 66 from the distal end toward the proximal end in the mentioned order.

As shown in FIG. 2A, the distal end hard portion 62 includes a main body 72 made of a transparent resin material and a connection tube 74 arranged at a proximal end of the main body 72. Each of the main body 72 and the connection tube 74 of the distal end hard portion 62 is formed into, e.g., a substantially cylindrical shape. A concave portion 72a where a distal end of the connection tube 74 is arranged is formed on an outer peripheral surface of the main body 72 of the distal end hard portion 62 on the proximal end side. Therefore, when the distal end of the connection tube 74 is arranged in the concave portion 72a on the proximal end side of the main body 72 of the distal end hard portion 62, arrangement of the main body 72 and the connection tube 74 can be positioned. It is to be noted that the main body 72 of the distal end hard portion 62 has non-conductive properties (insulation properties). On the other hand, it is preferable for the connection tube 74 to be made of a metal material such as a stainless steel material, and the connection tube 74 has conductive properties.

The bending portion 64 includes a bending tube 82 in which bending pieces (node rings) 82a, 82b, 82c, are aligned in an axial direction. In the bending piece 82a provided at the outermost distal end, a distal end of each of wires 84 which are used for bending the bending tube 82 is fixed to each wire fixing portion 84a. It is to be noted that each wire fixing portion 84a is formed by, e.g., pressing the bending piece 82a at the outermost distal end. Furthermore, each wire 84 is extended from the wire fixing portion 84a to the operation portion main body 42 of the operation portion 34 shown in FIG. 1, and a proximal end of each wire 84 is connected to the rotation portion 42b in the operation main body 42. Each wire 84 is covered with a coil tube 86 in the tubular portion 66. Therefore, when the bending operation knob 42a is operated, each wire 84 is moved in the axial direction through the rotation portion 42b, thereby freely bending the bending tube 82.

It is to be noted that each wire 84 is preferably formed of a strand made of a metal material and has conductive properties.

Additionally, an outer peripheral surface of the bending piece 82a, which is provided at the outermost distal end, of the bending tube 82 is fixed on an inner peripheral surface of the connection tube 74. The bending tube 82 having the respective bending pieces 82a, 82b, 82c, . . . is preferably made of a metal material such as a stainless steel material, and it has conductive properties. Here, the connection tube 74 and the bending tube 82 are fixed by a coupling portion 90 such as an adhesive having conductive properties or screws. FIG. 2A shows an example where both the connection tube 74 and the bending tube 82 are connected by using the later-described adhesive having conductive properties. When the coupling portion 90 is the adhesive, the connection tube 74 is fixed to the bending tube 82 by the adhesive applied on the circumference. That is, the connection tube 74 has conductive properties with respect to the bending tube 82, and the connection tube 74 and the bending tube 82 are electrically connected.

Therefore, the connection tube (a ground metal member) 74 of the distal end hard portion 62, the bending tube (a ground metal member) 82 and each wire (a ground metal member) 84 of the bending portion 64, and the rotation portion (a ground metal member) 42b in the operation portion main body 42 are electrically connected, and they have conductive properties. It is to be noted that the connection tube (the ground metal member) 74 of the distal end hard portion 62 and the bending tube (the ground metal member) 82 and each wire (the ground metal member) 84 of the bending portion 64 form a structure of the insertion portion 32. Therefore, these ground metal members do not additionally require a conductive wire or the like to achieve electrical conduction with respect to the ground metal members, whereby an increase in diameter of the insertion portion 32 can be avoided.

As shown in FIG. 3A, the rotation portion 42b is electrically connected through an electric cable EL1 to an electric cable L2 which is a signal line of later-described GND in the operation portion 34, for example, in the operation portion main body 42. Although it is preferable to electrically connect the rotation portion 42b to the electric cable L2 in the operation portion main body 42 of the operation portion 34, these members may be connected in the universal cord 44, in the light guide connector 46, in the video cable 48, or in the electrical connector 50.

Figure 2D:
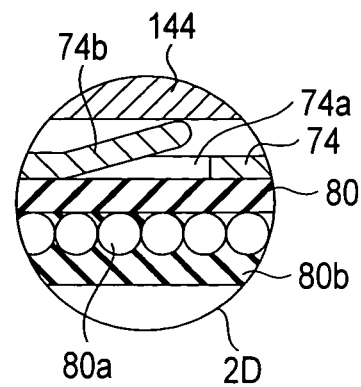
FIG. 2D is an enlarged longitudinal cross-sectional view indicated by reference sign 2D in FIG. 2A.

It is to be noted that the outer peripheral surface of the connection tube 74 of the distal end hard portion 62 and the outer peripheral surface of the bending tube 82 of the bending portion 64 are covered with a common outer tube 80. Since the outer tube 80 has insulating properties, electricity is prevented from flowing through the connection tube 74 or the bending tube 82 from the outer side of the insertion portion 32 in the radial direction. Moreover, as shown in FIG. 2A and FIG. 2D, a thread 80a is wound around the outer peripheral surface of the main body 72 of the distal end hard portion 62 and the outer peripheral surface of the outer tube 80, and an adhesive 80b is applied from the outer side of the thread 80a.

The tubular portion 66 shown in FIG. 1 and FIG. 2A is assumed to be a flexible tube in the embodiment. The tubular portion 66 includes a helical tube 92, a blade 94, and an outer tube 96. The helical tube 92 is preferably made of a metal material such as a stainless steel material, and it has conductive properties. Here, the bending tube 82 and the helical tube 92 are fixed by, e.g., an adhesive or screws having conductive properties. That is, the bending tube 82 has conductive properties with respect to the helical tube 92, and these members are electrically connected. It is to be noted that the bending tube 82 and the helical tube 92 may be connected by using a conductive connection tube (not shown) different from the connection tube 74.

Additionally, as shown in FIG. 3A, the helical tube 92 is electrically connected through an electric cable EL2 to the electric cable L2 which is the signal line of the later-described GND in the operation portion 34, for example, in the operation portion main body 42. Although it is preferable to electrically connect the helical tube 92 to the electric cable L2 in the operation portion main body 42 of the operation portion 34, these members may be electrically connected in the universal cord 44, in the light guide connector 46, in the video cable 48, or in the electrical connector 50.

It is to be noted that the connection tube (the ground metal member) 74 of the distal end hard portion 62, the bending tube (the ground metal member) 82 of the bending portion 64 and the helical tube (the ground metal member) 92 form a structure of the insertion portion 32. Therefore, these ground metal members do not additionally require a conductive cable or the like to achieve electrical conduction in the ground metal members, and an increase in diameter of the insertion portion 32 can be avoided.

In the insertion portion 32 and the operation portion 34 of the electronic endoscope 12, an illumination optical system 102 (see FIG. 2B and FIG. 2C) and an observation optical system 104 (see FIG. 2A to FIG. 2C) are arranged.

The illumination optical system 102 includes a light guide 112 having one end (a distal end) arranged in the distal end hard portion 62 of the insertion portion 32 and the other end (a proximal end) arranged in the light guide connector 46 of the operation portion 34. As shown in FIG. 2B, the one end of the light guide 112 according to this embodiment is arranged in each hole portion 72b formed in the main body 72 of the distal end hard portion 62. Further, the one end of the light guide 112 abuts on and is fixed to a non-illustrated R-shaped portion formed on a bottom portion of each hole portion 72b.

The light guide end portion 46a according to the embodiment can be connected to the concave portion 16a of the light source apparatus 16. Therefore, illumination light emitted from the light source apparatus 16 is transmitted through the light guide 112 from the concave portion 16 via the light guide end portion 46a, and the illumination light exits from the illumination optical system 102 in the distal end hard portion 62. At this time, the illumination light is widened by the R-shaped portion, and a wide range can be irradiated with the illumination light from the main body 72 of the distal end hard portion 62 made of a transparent resin. Therefore, a subject is illuminated.

In this manner, since the distal end of the light guide 112 abuts on the main body 72 without interposing a metal member in the main body 72 made of a resin material, a wall thickness corresponding to the metal member is not required, and a diameter of the distal end of the insertion portion 32 can be reduced.

As shown in FIG. 2A, the observation optical system 104 includes an objective lens unit 122, a solid-image image sensor unit 124, and an imaging cable 126. The objective lens unit 122 and the solid-state image sensor unit 124 are arranged in the distal end hard portion 62 of the insertion portion 32. It is to be noted that the objective lens unit 122 is arranged at the outermost distal end of the observation optical system 104, and the solid-state image sensor unit 124 is arranged at the proximal end of the objective lens unit 122. The imaging cable 126 has one end arranged at the proximal end of the solid-state image sensor unit 124 and the other end connected to the electrical connector 50. When the electrical connector 50 is connected to the video processor 14, an electrical signal output from an imaging element 148 in the distal end hard portion 62 of the insertion portion 32 can be displayed as a video picture in the monitor 20.

The objective lens unit 122 includes a first lens group (an optical element) 132 and a first holding frame (a frame member) 134 which holds the first lens group 132. The first holding frame 134 is inserted into and fixed in a through hole 72c of the main body 72 of the distal end hard portion 62, and the first holding frame 134 is at least partially exposed on the distal end surface of the main body 72 of the distal end hard portion 62. It is to be noted that the first holding frame 134 is preferably made of a metal material such as a stainless steel material, and it has conductive properties.

The solid-state image sensor unit 124 includes a second lens group (an optical element) 142, a second holding frame (a frame member) 144 that holds the first holding frame 134 and also holds the second lens group 142, a reinforcing frame (a frame member) 146 arranged on an outer peripheral portion of the second holding frame 144 at the proximal end, an imaging element (an optical element) 148 that is accommodated in the reinforcing frame 146 and connected to the second lens group 142, and an imaging substrate 150. It is to be noted that the second holding frame 144 is preferably made of a metal material such as a stainless steel material and it has conductive properties. Likewise, the reinforcing frame 146 is preferably made of a metal material such as stainless steel material and it has conductive properties. A space between the second holding frame 144 and the imaging element 148 and a space between the reinforcing frame 146 and the imaging element 148 are filed with an adhesive. Further, each of the reinforcing frame 146 and the second holding frame 144 does not usually have a configuration that actively achieves electrical conduction with the imaging element 148. However, the adhesive is not completely insulated since an air layer or the like is present in no small measure.

The electronic endoscope 12 enables electrical conduction between the connection tube (the ground metal member) 74 of the distal end hard portion 62 and at least one of a conductive member (e.g., the first holing frame 134) of the objective lens unit 122 and a conductive member (the second holding frame 144 or the reinforcing frame 146) of the solid-state image sensor unit 124.

Figure 2E:
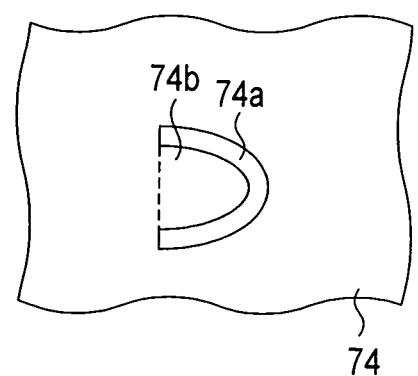
FIG. 2E is a schematic plan view showing a contact portion of a connection tube in the longitudinal cross-sectional view depicted in FIG. 2D.

In this embodiment, a substantially-U-like or substantially-crescent-like slit 74a is formed in the connection tube 74 of the distal end hard portion 62 as shown in FIG. 2E, and a tongue-like contact portion (a claw portion) 74b formed by the slit 74a is inwardly folded and brought into contact with the second holding frame 144 as shown in FIG. 2C and FIG. 2D. The contact portion 74b is folded toward the inner side along the radial direction of the connection tube 74 in advance, and the connection tube 74 is assembled to the main body 72 of the distal end hard portion 62 in this state. Therefore, the contact portion 74b comes into contact with the second holding frame 144, and electrical conduction is achieved between the connection tube 74 and the second holding frame 144. As a result, the electrical conduction between the conductive member (the second holding frame 144 or the reinforcing frame 146) of the solid-state image sensor unit 124 and the connection tube 74 can be assured by a relatively simple assembling operation. That is, the contact portion 74b functions as a conductive connecting portion. It is to be noted that, since the contact portion 74b is folded toward the inner side of the connection tube 74 made of, e.g., a metal material and thereby formed, it is possible to maintain a state that the contact portion 74b can be elastically deformed, has spring properties (biasing force), and is constantly in contact with the second holding frame 144.

It is to be noted that the second holding frame 144 of the solid-state image sensor unit 124 of the observation optical system 104 has an arbitrary outer shape, but arranging the second holding frame 144 and the connection tube 74 to be as close as possible is preferable so that a configuration for assuring the electrical conduction between the second holding frame 144 and the connection tube 74 of the distal end hard portion 62 can be easily adopted. The structure which arranges the second holding frame 144 and the contact portion 74b to be as close as possible can be easy to retain strength than the structure of the contact portion 74b formed on the connection tube 74. Therefore, an outer shape like a cockscomb which is thick in the vertical direction in FIG. 2C is adopted for the second holding frame 144, and the second holding frame 144 is arranged to be closer to the connection tube 74, i.e., the ground metal member. When the second holding frame 144 is symmetrically extended in opposite directions with the observation optical system 104 at the central axis, fabrication of the second holding frame 144 can be facilitated, which is preferable.

The imaging cable 126 is connected to a terminal arranged on the electrical connector 50 of the operation portion 34 through the insertion portion 32. Further, the electrical connector 50 is electrically connected to the video processor 14. In case of obtaining an image of the electronic endoscope 12, an image of an illuminated subject is taken in by the objective lens unit 122, the image is acquired by the solid-state image sensor unit 124 and converted into an electrical signal, the signal is supplied to the video processor 14 through the imaging cable 126, and a video picture is output to the monitor 20.

Here, as shown in FIG. 3A, the imaging cable 126 is a composite cable including 10 signal lines of vertical drive signals ($\phi$V1 to $\phi$V4), horizontal drive signals ($\phi$H1, $\phi$H2, $\phi$H), a video output signal (Vout), a power supply (VDD), and grounding (GND). Electric cables L1 and L2 are used for the signal lines of VDD and GND, and coaxial cables L3, ..., L10 are used for the other eight signal lines, respectively. Each of the vertical drive type signals $\phi$V1 and $\phi$V3 is a signal of a three-value pulse (High, Middle, Low) including a negative voltage (Low). Each of the vertical drive type signals $\phi$V2 and $\phi$V4 is a signal of a two-value pulse (Middle, Low) including a negative voltage (Low). Each of the horizontal drive type signals ($\phi$H1, $\phi$H2, $\phi$R) is a signal of a two-value pulse (High, Middle) including no negative voltage. Each of VDD and GND terminals of the solid-state image sensor unit 124 is connected to VDD and GND terminals of the video processor 14 through the electric cables L1 and L2, respectively. Terminals of the solid-state image sensor unit 124 for the vertical drive type signals ($\phi$V1 to $\phi$V4), the horizontal drive type signals ($\phi$H1, $\phi$H2, $\phi$R), and a video output signal (Vout) are connected to terminals of the video processor 14 for the vertical drive type signals ($\phi$V1 to $\phi$V4), the horizontal drive type signals ($\phi$H1, $\phi$H2, $\phi$R), and a video output signal (Vout) via core wires of coaxial cables L3, ..., L10. Further, in the vicinity of the solid-state image sensor unit 124, external conductors (shielded wires) of all the coaxial cables L3, ..., L10 are collectively connected to the electric cables L2 of GND. In the electrical connector 50, internal conductors (core wires) of the coaxial cables L3, ..., L6 of the vertical drive type signals ($\phi$V1 to $\phi$V4) are connected to the shielded wires through capacitors C1, ..., C4. Furthermore, in the electrical connector 50, the shielded wires of the coaxial cables L3, ..., L6 of the vertical drive type signals are collectively connected to the electric cable L2 of GND.

A configuration of the electrical connector 50 will now be described with reference to FIG. 3B.

Figure 3B:
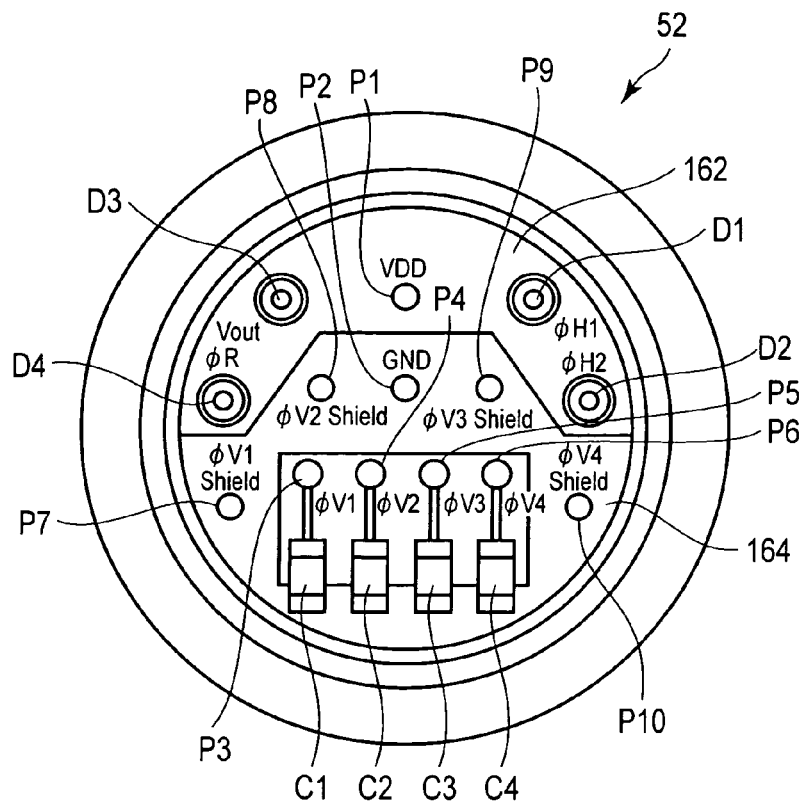
FIG. 3B is a schematic plan view showing a configuration of an electrical connector according to the first embodiment.

In a connector case 52 of the electrical connector 50 in FIG. 1, a substrate 162 shown in FIG. 3B is provided. To the substrate 162 are provided contact portions P1, ..., P10 and coaxial contacts D1, ..., D4.

The contact portions P1, ..., P10 are used for the core wires of VDD, GND, and the vertical drive signals and the shielded wires. That is, each of the contact portions P1 and P2 is connected to each of the electric cables L1 and L2, each of the contact portions P3, ..., P6 is connected to the core wire of each of the coaxial cables L3, ..., L10, and each of the contact portions P7, ..., P10 is connected to the shielded wire of each of the coaxial cables L3, ..., L6.

Each of internal contacts of the coaxial contacts D1, ..., D4 is connected to each core wire of the coaxial cables L7, ..., L10, and each of external contacts of the coaxial contacts D1, ..., D4 is provided on the outer periphery of each internal contact in an insulated manner and connected to each shielded wire of the coaxial cables L7, ..., L10.

The contact portions P7, ..., P10 of the shielded wires of the vertical drive signals and the contact portion P2 of GND are provided on a GND portion 164 on the substrate 164 with the same potential. It is desirable for the GND portion 164 to have an area which is as large as possible. The contact portions P3, ..., P6 of the core wires of the vertical drive signals are connected to the GND portion 164 through the capacitors C1, ..., C4 each of which is formed as a chip, respectively. As a result, the connection of the electrical connector 50 shown in FIG. 3A is realized.

According to such a configuration, in the electronic endoscope 12, the imaging cable 126 having the signal lines (the electric cables L1 and L2, and the coaxial cables L3, ..., L10) electrically connected to the solid-state image sensor unit 124 in the distal end portion of the insertion portion 32 is connected to an external contact portion through the electrical connector 50 of the operation portion 34.

In the electronic endoscope 12, the signal lines (the core wires of the coaxial cables L3, ..., L6) through which image sensor drive pulses including a negative voltage are transmitted in the signal lines in the imaging cable 126 are connected to a ground terminal of the image sensor unit 124 via the capacitors C1, ..., C4.

Therefore, each of the second holding frame 144 of the observation optical system 104, the connection tube 74 of the distal end hard portion 62 of the insertion portion 32, the bending tube 82 of the bending portion 64, the wires 84, and the rotation portion 42 which are provided between the main body 72 of the distal end hard portion 62 and the operation portion 34 is made of each metal member having conductive properties (which will be referred to as a ground metal member hereinafter), and these ground metal members are coupled and electrically connected with each other to achieve electrical conduction. Additionally, in a state where the electric cable EL1 is connected to the electric cable L2, when the electrical connector 50 is connected to the video processor 14, these ground metal members become electrically conductive with respect to a ground portion (GND) 14a of the video processor 14.

Further, each of the second holding frame 144 of the observation optical system 104, the connection tube 74 of the distal end hard portion 62 of the insertion portion 32, and the bending tube 82 of the bending portion 64 is formed of a metal member having conductive properties (which will be referred to as a ground metal member hereinafter), and these ground metal members are coupled and electrically connected with each other. Furthermore, in a state that the electric cable EL2 is connected to the electric cable L2, when the electrical connector 50 is connected to the video processor 14, these ground metal members become electrically conductive with respect to the ground portion (GND) 14a of the video processor 14.

Therefore, since the second holding frame 144 of the observation optical system 104, the connection tube 74 of the distal end hard portion 62 of the insertion portion 32, the bending tube 82 of the bending portion 64, the wires 84, the rotation portion 42b, the electric cable EL1, and the electric cable L2 are electrically connected these members have the same potential as the ground portion 14a of the video processor 14 in all regions from the distal end of the insertion portion 32 to the electrical connector 50. Likewise, since the second holding frame 144 of the observation optical system 104, the connection tube 74 of the distal end hard portion 62 of the insertion portion 32, the bending tube 82 of the bending portion 64, the electric cable EL2, and the electric cable L2 are electrically connected, these members have the same potential as the ground portion 14a of the video processor 14 in all regions from the distal end of the insertion portion 32 to the electrical connector 50. Furthermore, the first holding frame 134 and the reinforcing frame 146 electrically connected to the second holding frame 144 also have the same potential as the ground portion 14a of the video processor 14.

Here, assuming that the connection tube 74 is not electrically conductive with respect to the metal member of the solid-state image sensor unit 124, when a high-frequency treatment device is used together with the endoscope, a leak current applied to, e.g., the distal end of the insertion portion of the endoscope or static electricity is allowed to flow through the first holding frame 134 and also allowed to flow through the second holding frame 144 and the reinforcing frame 146. Then, electric charges that have nowhere to move may possibly jump to the solid-state image sensor 148. As a result, an inconvenience, e.g., mixing of noise may possibly occur in an image obtained by the endoscope.

On the other hand, as described above, when the second holding frame 144 is allowed to have the same potential as the ground portion 14a of the video processor 14, since the second holding frame 144 is electrically connected to the first holding frame 134, a current allowed to flow through, e.g., the distal end of the insertion portion 32 flows through the ground portion 14a of the video processor 14. As a result, an intended current can be prevented from flowing through the solid-state image sensor 148, and an electrical influence, e.g., mixing noise in an image obtained by the electronic endoscope 12 can be avoided.

Therefore, when both the electronic endoscope 12 and the high-frequency treatment device (not shown) are used or when static electricity (electric charges) is unexpectedly applied to the distal end, an image obtained by the electronic endoscope 12 can be prevented from being electrically affected by allowing a current to flow through the ground metal (GND) without allowing the current flowing through the image sensing device 148.

Further, for example, in Jpn. Appln. KOKAI Publication No. 2007-89888, a conductive wire for electrical conduction of an imaging cable is disposed to a CCD holding frame. That is, an outer diameter of an insertion portion must be increased for the conductive wire. On the other hand, in this embodiment, the second holding frame (the CCD holding frame) 144 does not have to be connected to the conductive wire in the insertion portion 32. Therefore, an influence on the outer diameter of the insertion portion 32 can be suppressed, and the diameter can be decreased.

It is to be noted that the rotation portion 42b is electrically connected to the electric cable EL1 in the foregoing embodiment, but the shaft portion 42c may be electrically connected to the electric cable EL1 in place of the rotation portion 42b.

Furthermore, in this embodiment, the helical tube 92 is electrically connected to the connection tube 74 and the bending tube 82 and also electrically connected to the electric cable L2 through the electric cable EL2, but the helical tube 92 may be made of a material having insulating properties. In this case, since the wires 84 have the conductive properties, a current that affects the solid-state image sensor unit 124 can be prevented from flowing.

It is to be noted that FIG. 2C shows a state that the two contact portions 74b are formed to face each other, the number of the contact portions 74b is not restricted to two, and one or more (e.g., three or above) contact portions 74b may be formed.

Moreover, in this embodiment, although the description has been given as to a case that the electric cables EL1 and EL2 are connected to the electric cable L2 of the imaging cable 126 in the operation portion 34 and further connected to the ground portion 14a of the video processor 14, the electric cables EL1 and EL2 may be directly connected to the ground portion 14a of the video processor 14 without interposing the electric cable L2 of the imaging cable 126. For example, a connectable electric cable may be directly connected to the ground portion 14a of each wire 84.

A second embodiment will now be described with reference to FIG. 4. This embodiment is a modification of the first embodiment, and like reference numerals denote members equal to those explained in the first embodiment to omit a detailed description thereof. This can be also applied to the later-described third and fourth embodiments.

In this embodiment, in place of forming the tongue-like contact portion 74b (see FIG. 2B and FIG. 2C) on the connection tube 74, a protrusion (a contact portion) 74c which is electrically connected to the connection tube 74 and has conductive properties is formed to protrude toward the inner side of the connection tube 74 along a radial direction. Moreover, the protrusion 74c is formed to sandwich a second holding frame 144 of a solid-state image sensor unit 124 of an observation optical system 104.

As described above, according to the configuration where the protrusion 74c having a function of a conductive connecting portion abuts on the second holding frame 144, as compared with the tongue-like contact portion 74b described in the first embodiment, the operation of folding the contact portion 74b can be omitted, and a lead time of assembling can be described, thereby improving work efficiency.

Figure 4:
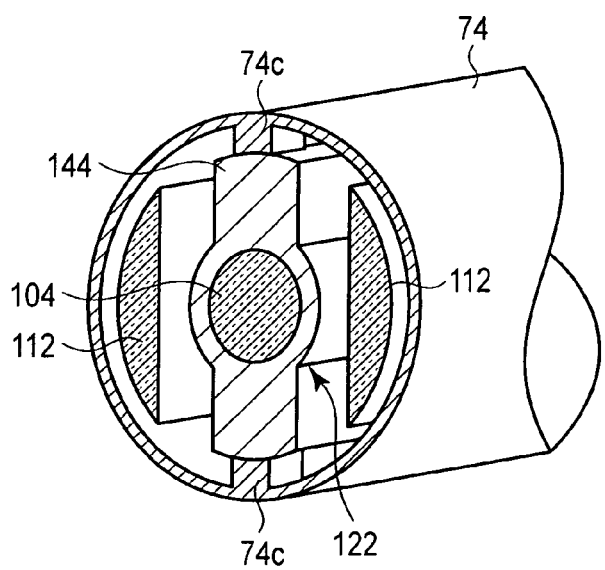
FIG. 4 is a schematic perspective view showing a state where a main body of a distal end hard portion is removed from a distal end of an insertion portion of an endoscope in an endoscopic system according to a second embodiment.

It is to be noted that an outer tube 80 (see FIG. 2A) which is not actually shown is arranged on an outer periphery of the connection tube 74 depicted in FIG. 4.

A third embodiment will now be described with reference to FIG. 5.

Figure 5:
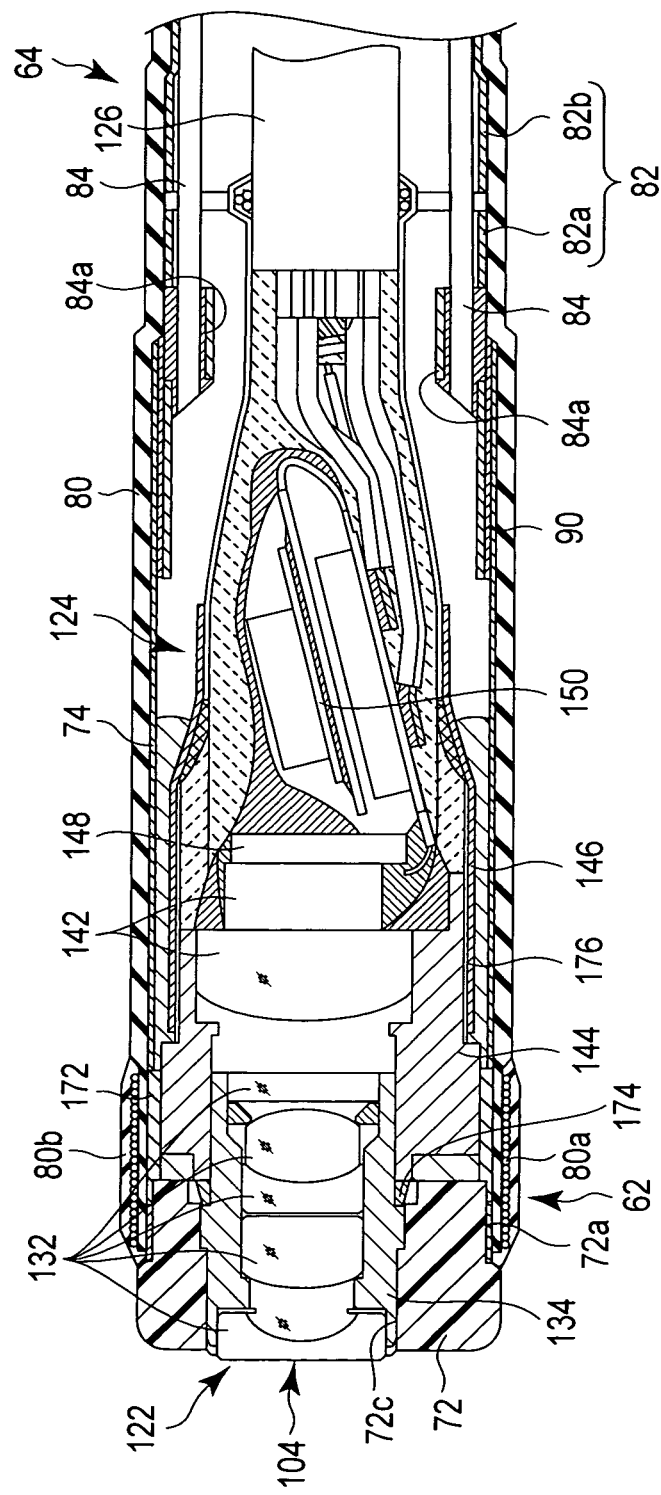
FIG. 5 is a longitudinal cross-sectional view of an insertion portion of an endoscope in an endoscopic system according to a third embodiment.

As shown in FIG. 5, an adhesive 172 having conductive properties is applied between a connection tube 74 and a second holding frame 144 of a solid-state image sensor unit 124 of an observation optical system 104, and an adhesive 174 having conductive properties is applied between the second holding frame 144 and a first holding frame 134 of an objective lens unit 122. Additionally, an adhesive 176 having conductive properties is applied between the second holding frame 144 and a reinforcing frame 146. It is preferable to use the same adhesive as these adhesives 172, 174, and 176. Therefore, the connection tube 74, the first holding frame 134, the second holding frame 144, and the reinforcing frame 146 are electrically connected, and electrical conduction can be assured between these members.

In addition, as an example of the adhesives (conductive connecting portions) 172, 174, and 176 having conductive properties, there is a material obtained by mixing silver in an epoxy-based adhesive.

In this embodiment, since the connection tube 74, the first holding frame 134, the second holding frame 144, and the reinforcing frame 146 are connected by just using the adhesives 172, 174, and 176 having conductive properties, it is possible to reduce stress on the second holding frame 144 of the solid-state image sensor unit 124 which is applied when the contact portion 74b or the protrusion 74c of the connection tube 74 abuts like the first embodiment or the second embodiment. Therefore, a constant burden imposed on the solid-state image sensor unit 124 by external force can be alleviated.

Further, it is also preferable to use the adhesives 172, 174, and 176 according to this embodiment together with the contact portion 74b of the connection tube 74 described in the first embodiment and/or together with the protrusion 74c of the connection tube 74 described in the second embodiment. Likewise, it is also preferable to apply the adhesive 174 having conductive properties at least one of between a pin member 182 as a conductive member which will be explained in a later-described fourth embodiment and the first holding frame 134, and between the pin member 182 and the second holding frame 144.

The fourth embodiment will now be described with reference to FIG. 6.

Figure 6:
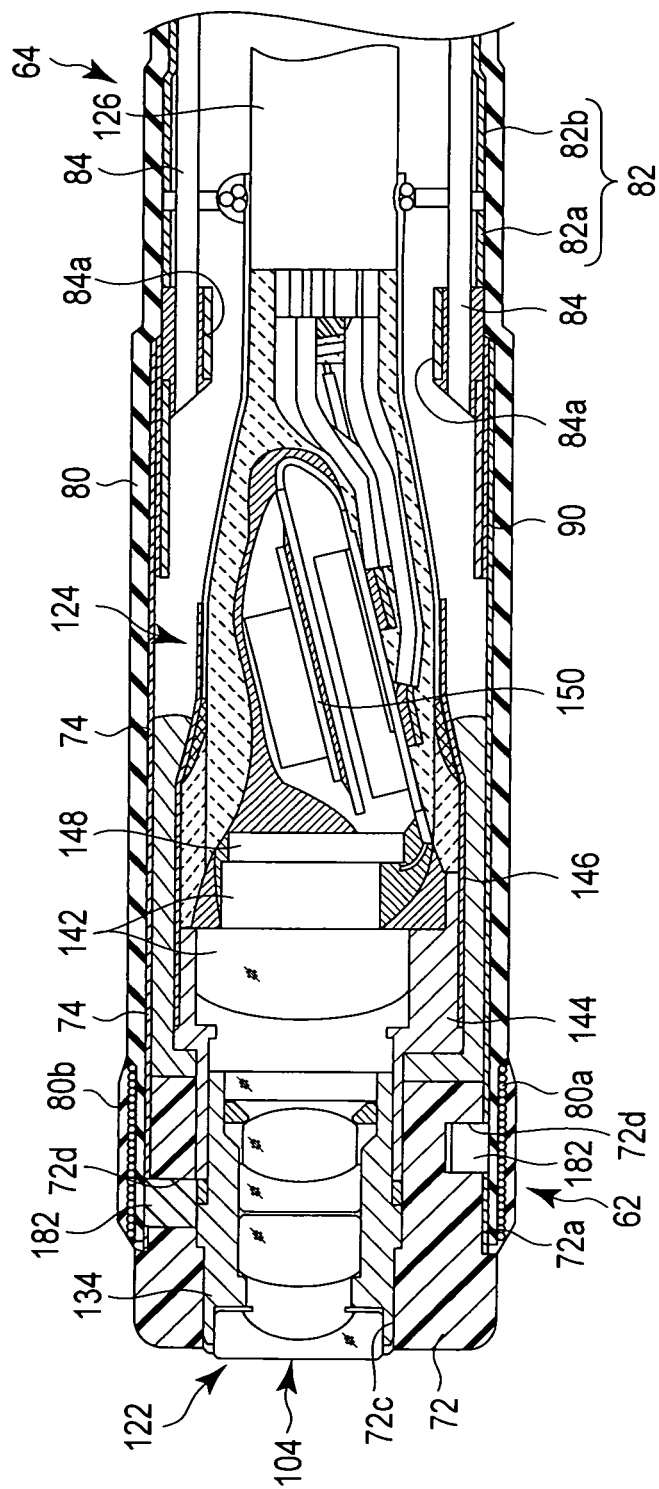
FIG. 6 is a schematic longitudinal cross-sectional view of an insertion portion of an endoscope in an endoscopic system according to a fourth embodiment.

As shown in FIG. 6, a through hole 72d is formed in a main body 72 of a distal end hared portion 62 from the outside in a radial direction. Further, a pin member (a conductive connecting portion) 182 which is preferably made of a metal material and has conductive properties is inserted into this through hole 72d. In the pin member 182 shown in FIG. 6, its end portion on the inner side along the radial direction abuts on at least one of a first holding frame 134 and a second holding frame 144 of a solid-state image sensor unit 124. Furthermore, when an end portion of the pin member 182 on the outer side along the radial direction is in contact with a connection tube 74, electrical conduction can be assured between the first and second holding frames 134 and 144 of the solid-state image sensor unit 124 and the connection tube 74.

In addition, it is preferable to assure the electrical conduction with respect to the connection tube 74 by forming the pin member 182 to slightly protrude from the connection tube 74 toward the outer side in the radial direction and performing, e.g., filing with respect to the pin member 182 together with the outer peripheral surface of the connection tube 74.

Meanwhile, an outer shape of the second holding frame 144 of the solid-state image sensor unit 124 of the observation optical system 104 on the distal end side according to this embodiment is formed into a cylindrical shape. That is, the second holding frame 144 according to this embodiment has a shape different from that of the second holding frame 144 described in each of the first to third embodiments. In this embodiment, as different from the contact portion 74b, the protrusion 74c, and the adhesive 172 described in the first to third embodiments, the second holding frame 144 does not have to approximate the connection tube 74. Therefore, the vertically thick portion adopted in the second holding frame 144 according to each of the first to third embodiments can be eliminated, and the portion which is thick in the vertical direction is substituted by the pin member 82. Therefore, the second holding frame 144 according to this embodiment can be easily processed as compared with the first to third embodiments. Therefore, molding of the first holding frame 134 which is fitted to the second holding frame 144 and of the main body 72 of the distal end hard portion 62 can be simpler than those described in the first to third embodiments.

A preferred configuration of a light guide 112 will now be described.

Figure 7A:
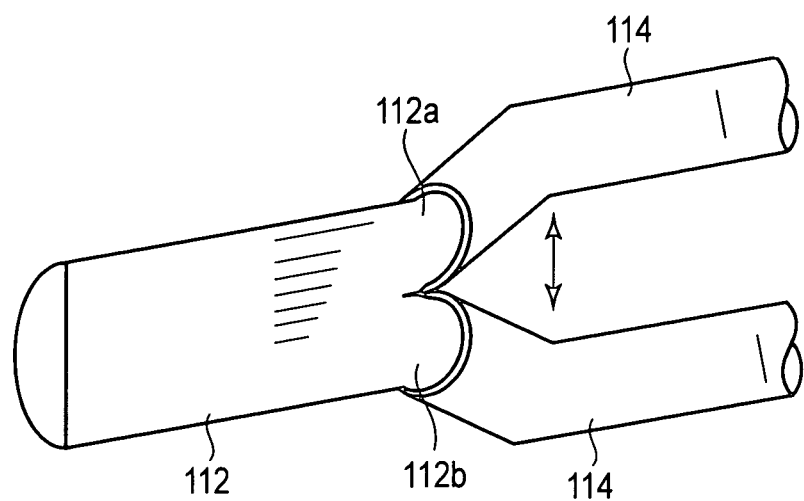
FIG. 7A is a schematic perspective view showing a light guide for use in the endoscope of the endoscopic system according to each of the first to fourth embodiments.
Figure 7B:
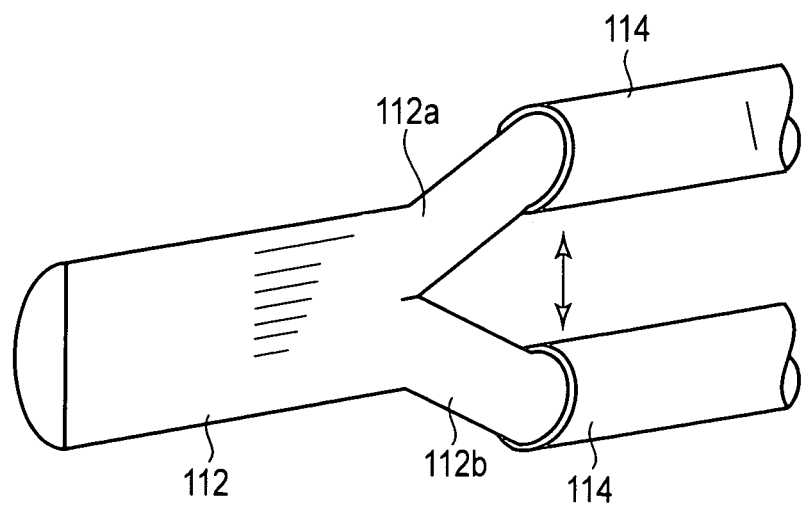
FIG. 7B is a schematic perspective view showing the light guide for use in the endoscope of the endoscopic system according to each of the first to fourth embodiments.

As shown in FIG. 7A and FIG. 7B, the light guide 112 is formed in such a manner that its portion near the distal end portion has a substantially semicircular transverse cross section from the distal end toward the proximal end side. That is, as shown in FIG. 2B, the vertical direction of the light guide 112 is formed longer than the transverse direction. Therefore, as compared with a situation where a light guide which has the same cross-sectional area and a circular cross section is arranged in the main body 72 of the distal end hard portion 62, an outer diameter of the main body 72 of the distal end hard portion 62 in the insertion portion 32 can be reduced.

It is preferable for the light guide 112 to bifurcate into two branches (two pieces) denoted by reference numerals 112a and 112b in FIG. 7A and FIG. 7B. It is preferable for a transverse cross section of the bifurcated portions designated by reference numerals 112a and 112b to be formed into a circular shape, and outer peripheral surfaces of the light guides 112a and 112b are covered with protective tubes 114, respectively. It is preferable to use, e.g., a nylon-based or silicon-based resin for the protective tube 114.

Additionally, as the protective tube 114, a tube having light permeability and a light color is preferably used. Then, when the light guide 112 has a portion at which the light guide is bent in the protective tube at a time of guiding light, then the light leaks from the side surface, thereby achieving identification of a bent position of each of the light guides 112a and 112b.

It is to be noted that FIG. 7A shows a state that the protective tube 114 covers even a position close to a root of the bifurcation, and FIG. 7B shows a state that the protective tube 114 covers the rear end side of the position close to the root. Moreover, the light guide 112 is molded to separate portions denoted by reference numerals 112a and 112b.

When the light guide is not formed to separate the portions denoted by reference numerals 112a and 112b (a situation where bifurcated bundles are alighted in a straight manner), the light guide is apt to be arranged and readily sandwiched between a rivet 83a of the bending tube 82 and the imaging cable 126. Therefore, it is difficult to prevent large force from being applied to the light guide.

Figure 8:
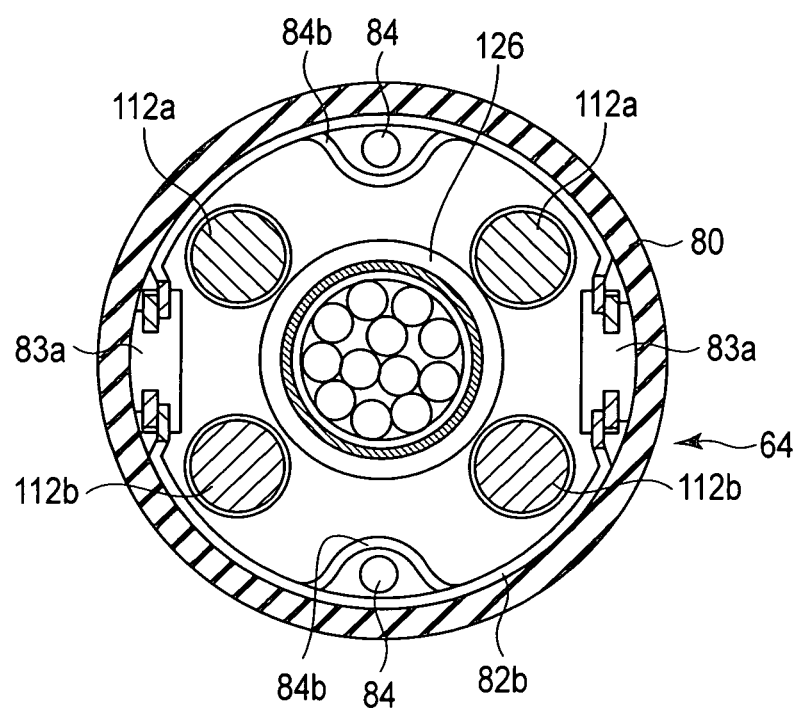
FIG. 8 is a schematic transverse cross-sectional view of a bending portion of the insertion portion of the endoscope in the endoscopic system according to each of the first to fourth embodiments.

On the other hand, as shown in FIG. 7A and FIG. 7B, when each of the pair of light guides 112 is bifurcated and molded to have two portions denoted by reference numerals 112a and 112b, the light guides 112a and 112b are arranged in the bending portion 64 as shown in FIG. 8. Therefore, when each light guide 112 is sandwiched between the rivet 83a of the bending tube 82 and the imaging cable 126, the portions of each light guide 112 denoted by reference numerals 112a and 112b can be moved to transfer force applied to the light guide 112. Therefore, it is possible to prevent fibers forming each light guide 112 from being folded when a great deal of force is applied to the light guide 112.

Furthermore, as shown in FIG. 8, each string guide 84b of the bending tube 82 into which the wire 84 is inserted is placed at a median position in the vertical direction. As a result, the light guides 112a and 112b can be symmetrically arranged with, e.g., the imaging cable 126 at the center. That is, when each of the light guides 112a and 112b is formed into the above-described shape, the built-in members in the bending tube 82 can be symmetrically aligned. Therefore, the internal space of the insertion portion 32 can be uniformly used, and interference of the built-in members can be alleviated.

As shown in FIG. 9A and FIG. 9B, in the vicinity of the position at which each light guide 112 is bifurcated, outer peripheral surfaces of the bifurcated light guides 112a and 112b are covered with a covering tube 114. In the vicinity of the position at which each light guide 112 is bifurcated, surfaces of the light guides 112a and 112b on the side close to the connection tube 74 have an arc shape including the two light guides 112a and 112b, and surfaces of the same on the side apart from the connection tube 74 are formed along, e.g., an outer shape of the first holding frame 134 of the observation optical system 104. Therefore, since a dead space can be reduced while maintaining areas of the light guides 112a and 112b, the outer diameter of the distal end hard portion 62 of the insertion portion 32 can be further decreased.

FIG. 10A and FIG. 10B show the distal end side of the insertion portion 32 apart from the position depicted in FIG. 9B. That is, each light guide 112 in FIG. 10A and FIG. 10B is associated with each position denoted by reference numeral 112 in FIG. 9A.

As shown in FIG. 10A, a surface of each light guide 112 on the side close to the connection tube 74 has an arc shape, and a surface of the same on the side apart from the connection tube 74 is formed along, e.g., an outer shape of the second holding frame 144 of the observation optical system 104. In this case, since the second holding frame 144 has a substantially L-like portion 144a, the light guide 112 also has a substantially L-like portion 112c.

As shown in FIG. 10B, a surface of the each light guide 112 on the side close to the connection tube 74 has an arc shape, and a surface of the same on the side apart from the connection tube 74 likewise has an arc shape along, e.g., the outer shape of the second holding frame 144 of the observation optical system 104. In this case, since the second holding frame 144 has an arc-like portion 144b, the light guide 112 also has an arc-like portion 112d.

Therefore, a dead space can be reduced while maintaining an area of each light guide 112, and hence the outer diameter of the distal end hared portion 62 of the insertion portion 32 can be further decreased.

Figure 11:
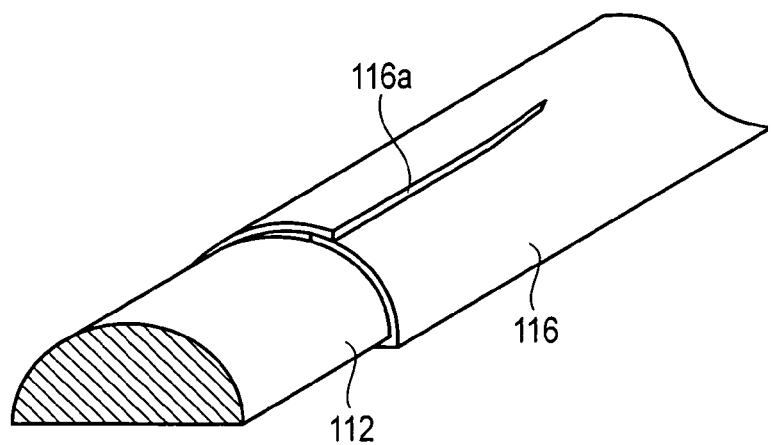
FIG. 11 is a schematic perspective view showing a state that the light guide is covered with a covering tube having a notch.

Furthermore, as shown in FIG. 11, each light guide 112 is covered with a protective tube 116. This covering tube 116 is molded into a state that a notch 116a is formed on a distal end side thereof. Therefore, a circumferential length of the protective tube 116 on the distal end side can be variable. Accordingly, the shape of the molded light guide 112 can be further closely covered with the protective tube 116. That is, the contact when the protective tube 116 is appressed against the outer peripheral surface of the light guide 112 can be enhanced. Therefore, the protective tube 116 can be prevented from being displaced toward the rear end side of the light guide 112. Moreover, a diameter of the protective tube 116 can be reduced, and the diameter of the distal end of the insertion portion 32 in the electronic endoscope 12 can be thereby decreased.

Figure 12:
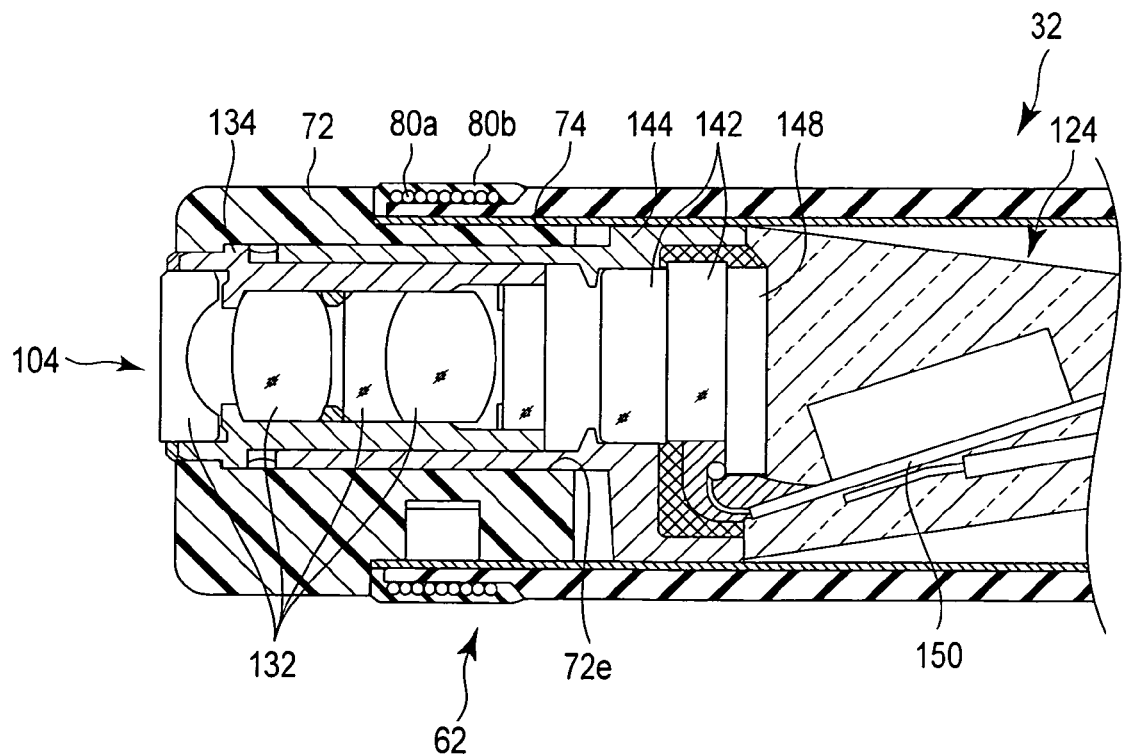
FIG. 12 is a schematic longitudinal cross-sectional view of an insertion portion of an endoscope having formed into a shape different from those according to the first to fourth embodiments.

In each of FIG. 2A, FIG. 5, and FIG. 6, the main body 72 of the distal end hard portion 62 is in contact with and fitted to the first holing frame 134 of the solid-state image sensor unit 124. In FIG. 12, on the contrary, the main body 72 of the distal end hard portion 62 is in contact with and fitted to the second holding frame 144 of the solid-state image sensor unit 124.

The second holding frame 144 of the observation optical system 104 is fitted in a hole portion 72e of the main body 72 of the distal end hard portion 62. In this case, as compared with a case where the first holding frame 134 is fitted with respect to the main body 72 of the distal end hard portion 62, an inclination at the time of assembling the first holding frame 134 and the second holding frame 144 affects an inclination of the main body 72 and the solid-state image sensor unit 124. Accordingly, the inclination produced by assembling the main body 72 with respect to the solid-state image sensor unit 124 can be alleviated. Therefore, it is possible to eventually reduce the inclination between the light guide 112, which is assembled to the main body 72, and the solid-state image sensor unit 124. Thus, interference of the light guide 112 and the observation optical system 104 caused due to the inclination of the observation optical system 104 in the insertion portion 32 can be alleviated, and it is possible to avoid folding of the fibers of each light guide 112 caused due to, e.g., the pressure of the solid-state image sensor unit 124.

Reference Embodiment

A reference embodiment of the endoscope 12 will now be described with reference to FIG. 13 to FIG. 16B. It is to be noted that this reference embodiment is a modification of each of the foregoing embodiments, and like reference numerals denote like members or members having like functions in the foregoing embodiments as far as possible, and a detailed description thereof will be omitted.

As shown in FIG. 13 to FIG. 16B, an illumination optical system 102, an observation optical system 104, and a channel tube 106 are arranged in an insertion portion 32 of an endoscope 12 according to this reference embodiment.

The illumination optical system 102 includes a pair of light guides 212a and 212b each having a substantially circular transverse cross section shown in FIG. 14A and FIG. 14B. The observation optical system 104 includes an objective lens unit 122, a solid-state image sensor unit (an imaging portion) 124 having, e.g., a substantially rectangular transverse cross section shown in FIG. 14A, and an imaging cable 126 having, e.g., a substantially circular transverse cross section shown in FIG. 15A. In this reference embodiment, the light guide 212a is arranged between a U direction and an L direction, the light guide 212b is arranged between a D direction and an R direction, the solid-state image sensor unit 124 is arranged between the D direction and the L direction, and the channel tube 106 is arranged between the U direction and the R direction with respect to a center axis C of a bending portion 64.

It is to be noted that an area of the transverse cross section of the solid-state image sensor unit 124 shown in FIG. 14A is larger than an area of the transverse cross section of the imaging cable 126 depicted in FIG. 15A. That is, the imaging cable 126 in the observation optical system 104 is formed smaller than that the solid-state image sensor unit 124.

The bending portion 64 of the insertion portion 32 includes an outer tube 80 and a bending tube 82. In this reference embodiment, a blade (a reticular tube) 81 is arranged between the outer tube 80 and the bending tube 82.

The bending tube 82 includes bending pieces (node rings) $82a, 82b, 82c, \ldots, 82_{m-1}, 82_m, 82_{m+1}, \ldots, 82_{n-2}, 82_{n-1}$, and $82_n$ and rivets $83a, 83b, \ldots, 83_{m-2}, 83_{m-1}, 83_m, \ldots, 83_{n-2}$, and $83_{n-1}$ each of which couples the bending pieces adjacent to each other to allow their rotational movement. The bending piece $82a$ at the outermost proximal end is fitted and fixed to a distal end hard portion 62. The bending piece $82_n$ at the outer proximal end is fitted and fixed to a connecting portion 222 between itself and a tubular portion 66. Moreover, in this reference embodiment, an intermediate bending piece $82_m$ is set down between the bending piece $82a$ provided at the outermost distal end and the bending piece $82_n$ at the outermost proximal end in the bending tube 82. It is to be noted that the intermediate bending piece $82_m$ may be provided at a position closer to the distal end side apart from the intermediate position or at a position closer to the proximal end side apart from the intermediate position in the bending tube 82.

In each of the bending pieces $82a, 82b, 82c, \ldots, 82_{m-1}, 82_m, 82_{m+1}, \ldots, 82_{n-2}, 82_{n-1}$, and $82_n$, wire guides (string guides) 236 into which angle wires 232a and 232b in the U direction and the D direction and angle wires 234a and 234b in the R direction and the L direction are inserted protrude from the inner peripheral surface of each bending piece toward the center axis C.

Figure 13:
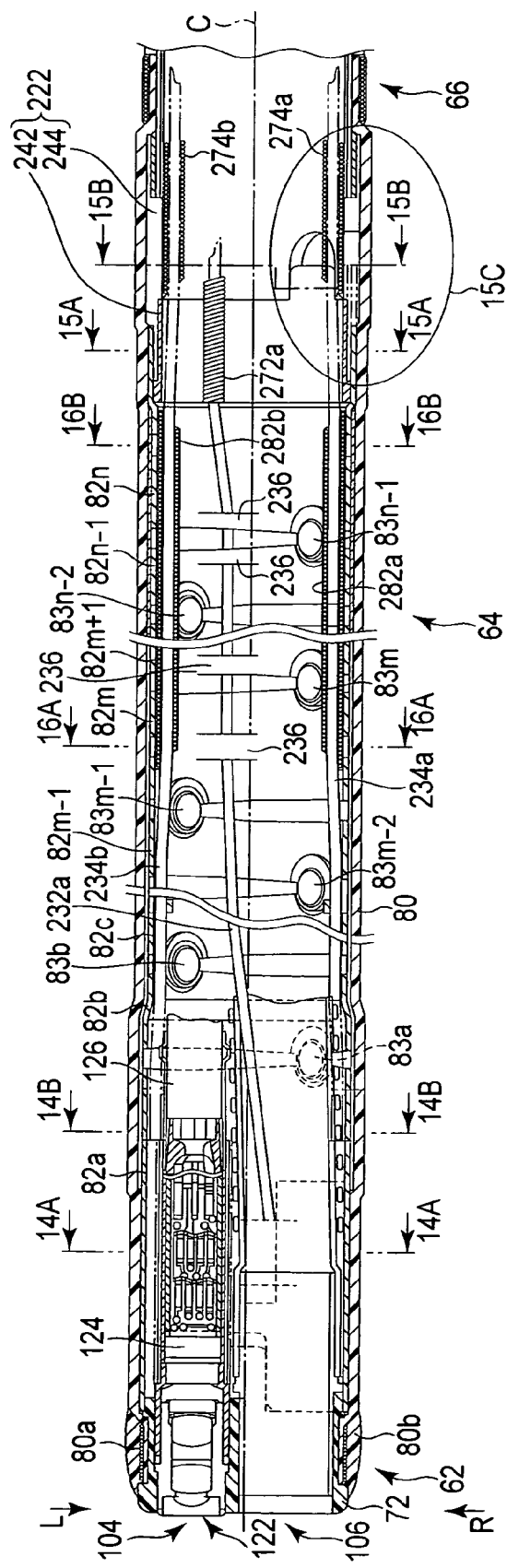
FIG. 13 is a schematic longitudinal cross-sectional view of an insertion portion of an endoscope according to a reference embodiment.

As shown in FIG. 13 and FIG. 14A, the angle wires 232a and 232b in the U direction and the D direction are brazed and fixed on the inner peripheral surface of the node ring 82a provided at the outermost distal end in the bending tube 82. As shown in FIG. 14A, the inner side of each wire guide 236 is formed as each of brazing and fixing portions 238a and 238b at the distal end of each of the angle wires 232a and 232b, whereby the angle wires 232a and 232b are fixed.

As shown in FIG. 13 and FIG. 14B, the angle wires 234a and 234b in the R direction and the L direction are brazed and fixed on the inner peripheral surface of the node ring 82a provided at a position on the proximal end side of positions where the angle wires 232a and 232b in the U direction and the D direction are brazed. As shown in FIG. 14B, the inner side of each wire guide 236 is formed as each of brazing and fixing portions 240a and 240b at the distal end of each of the angle wires 234a and 234b, whereby the angle wires 234a and 234b are fixed.

That is, the angle wires 232a and 232b in the U direction and the D direction are fixed at positions where they are substantially opposed to each other with respect to the center axis C, the angle wires 234a and 234b in the R direction and the L direction are fixed at positions where they are substantially opposed to each other with respect to the center axis C, the angle wires 234a and 234b in the R direction and the L direction are fixed at rear positions along the center axis C with respect to the angle wire 232a in the U direction, and the angle wires 234a and 234b in the R direction and the L direction are fixed at rear positions along the center axis C with respect to the angle wire 232b in the D direction. As described above, the fixed positions of the angle wire 232a in the U direction, the angle wire 232b in the D direction, the angle wire 234a in the R direction, and the angle wire 234b in the L direction with respect to the node ring 82a are apart from each other. Therefore, it is possible to suppress transfer of heat from the angle wire, which is being brazed with respect to the bending piece 82a, to the angle wire, which has been already fixed to the bending piece 82a. That is, it is possible to suppress occurrence of a thermal impact on the angle wire which has been already fixed to the bending piece 82a.

Furthermore, as described above, in the observation optical system 104, the transverse cross section of the imaging cable 126 has a smaller occupied area than the transverse cross section of the solid-state image sensor unit 124. Therefore, in the node ring 82a provided at the outermost distal end, positions at which the distal ends of the angle wires 232a and 232b in the U direction and the D direction are brazed (the brazing and fixing portions 238a and 238b) are set to positions facing the solid-state image sensor unit 124, positions at which the distal ends of the angle wires 234a and 234b in the R direction and the L direction are brazed (the brazing and fixing portions 240a and 240b) are set to positions facing the imaging cable 126, these positions are displaced along a front-and-back direction in the bending piece 82a provided at the outermost distal end, and hence a space for brazing can be readily assured. Thus, in the bending portion 64 having the bending piece 82a which has relatively small outer and inner diameters, the distal ends of the angles wires 232a, 232b, 234a, and 234b can be further readily fixed.

As described above, the connecting portion 222 is arranged between the bending portion 64 and a tubular portion 66. The connecting portion 222 includes a first connection tube 242 and a second connection tube 244. It is to be noted that the first connection tube 242 and the second connection tube 244 are bonded and fixed to each other by using, e.g., an adhesive.

As shown in FIG. 13 and FIG. 15C, the first connection tube 242 includes a cylindrical portion 252 and an outward flange portion 254 provided at a distal end of the cylindrical portion 252. The second connection tube 244 includes a main body cylindrical portion 262, a distal end-side thin cylindrical portion 264 which is provided at a distal end of the main body cylindrical portion 262 and has a cylindrical shape, and a proximal end-side thin cylindrical portion 266 which is provided at a proximal end of the main body cylindrical portion 262 and has a cylindrical shape. An inner abutting portion 262a on which the proximal end of the cylindrical portion 252 of the first connection tube 242 abuts is formed on the inner peripheral side at the distal end of the main body cylindrical portion 262. An outer abutting portion 262b on which the proximal end of the node ring $82_n$ on the outermost proximal end side in the bending tube 82 of the bending portion 64 abuts is formed on the outer peripheral side at the distal end of the main body cylindrical portion 262. It is preferable to form the inner peripheral surface of the first connection tube 242 and the inner peripheral tube of the second connection tube 244 so that these surfaces can be level or substantially level with each other when the proximal end of the cylindrical portion 252 of the first connection tube 242 is fitted to the inner abutting portion 266 of the main body cylindrical portion 262 of the second connection tube 244.

It is to be noted that an inner abutting portion 262c on which the distal end of, e.g., a helical tube 66a of the tubular portion 66 abuts is formed on the inner peripheral side at the proximal end of the main body cylindrical portion 262.

As shown in FIG. 15A, distal ends of coil tubes 272a and 272b in the U direction and the D direction are fixed by, e.g., brazing on the inner peripheral surface of the cylindrical portion 252 of the first connection tube 242 preferably from the distal end to the proximal end. That is, as shown in FIG. 15A, the inner side of the first connection tube 242 of the connecting portion 222 is formed as each of brazing and fixing portions 276a and 276b for the distal end of each of the coil tubes 272a and 272b in the U direction and the R direction, whereby the coil tubes 272a and 272b are fixed.

As shown in FIG. 15B, distal ends of coil tubes 274a and 274b in the R direction and the L direction are fixed by, e.g., brazing on the inner peripheral surface of the main body cylindrical portion 262 of the second connection tube 244 preferably from the distal end to the proximal end. That is, as shown in FIG. 15B, the inner side of the second connection tube 244 of the connecting portion 222 is formed as each of brazing and fixing portions 278a and 278b for the distal end of each of the coil tubes 274a and 274b in the R direction and the L direction, whereby the coil tubes 274a and 274b are fixed.

It is to be noted that the angle wire 232a in the U direction is inserted into the coil tube 272a in the U direction, the angle wire 232b in the D direction is inserted into the coil tube 272b in the D direction, the angle wire 234a in the R direction is inserted into the coil tube 274a in the R direction, and the angle wire 234b in the L direction is inserted into the coil tube 274b in the L direction.

As shown in FIG. 15A, the coil tubes 272a and 272b in the U direction and the D direction are fixed at the positions where these tubes are opposed to each other with respect to the center axis C. Therefore, the positions at which the coil tubes 272a and 272b are disposed are far positions on the inner peripheral surface of the cylindrical portion 252 of the first connection tube 242, and it is possible to suppress transfer of heat from the coil tube 272b, which is being brazed to the inner peripheral surface of the cylindrical portion 252 of the first connection tube 242, to the coil tube 272a, which has been already fixed on the inner peripheral surface of the cylindrical portion 252. Therefore, it is possible to suppress occurrence of a thermal impact on the coil tube 272 which has been already fixed on the cylindrical portion 252 of the first connection tube 242.

As shown in FIG. 15B, the coil tubes 274a and 274b in the R direction and the L direction are fixed at the positions where these tubes are substantially opposed to each other with respect to the center axis C. Therefore, the positions at which the coil tubes 274a and 274b are disposed are far positions on the inner peripheral surface of the main body cylindrical portion 262 of the second connection tube 244, and it is possible to suppress transfer of heat from the coil tube 274b, which is being brazed to the inner peripheral surface of the main body cylindrical portion 262 of the second connection tube 244, to the coil tube 274a, which has been already fixed on the inner peripheral surface of the main body cylindrical portion 262. Therefore, it is possible to suppress occurrence of a thermal impact on the coil tube 274a which has been already fixed on the main body cylindrical portion 262 of the second connection tube 244.

Additionally, the coil tubes 272a and 272b are disposed on the inner peripheral surface of the cylindrical portion 252 of the first connection tube 242, the coil tubes 274a and 274b on the inner peripheral surface of the main body cylindrical portion 262 of the second connection tube 244, and then the first connection tube 242 and the second connection tube 244 are fixed. At this time, the first connection tube 242 is arranged on the side close to the distal end of the insertion portion 32, the second connection tube 244 is arranged on the side close to the proximal end of the insertion portion 32 of the second connection tube 244, and the main body cylindrical portion 262 of the second connection tube 244 is arranged on the outer side of the cylindrical portion 252 of the first connection tube 242. The outward flange portion 254 of the first connection tube 242 abuts on the distal end of the thin cylindrical portion 264 of the second connection tube 244. The proximal end of the cylindrical portion 252 of the first connection tube 242 abuts on the inner abutting portion 266 of the second connection tube 244. Further, the outer peripheral surface of the first connection tube 242 and the inner peripheral surface of the second connection tube 244 are fitted, bonded, and fixed to each other.

It is to be noted that the proximal end of the bending piece $82_n$ provided on the outermost proximal end side is arranged on the outer peripheries of the first connection tube 242 and the second connection tube 244.

As described above, the distal ends of each pair of the coil tubes 272a, 272b, 274a, and 274b which are opposed to each other are arranged on the first and second connection tubes 242 and 244, respectively, thus, a thermal impact can be avoided, and the connection unit 222 obtained by assembling the first and second connection tubes 242 and 244 can be easily formed.

As shown in FIG. 13 and FIG. 16A, the distal ends of the coil pipes 282a and 282b, which are preferably closely wound, are fixed on the inner peripheral surface of the intermediate bending piece $82_m$ by, e.g., bonding or brazing. That is, as shown in FIG. 16A, the inner peripheral surface of the intermediate bending piece $82_m$ is formed as fixing portions 284a and 284b for the distal ends of the coil pipes 282a and 282b in the R direction and the L direction, whereby the coil pipes 282a and 282b are fixed.

As shown in FIG. 13 and FIG. 16B, the proximal ends of the coil pipes 282a and 282b, which are preferably closely wound, are fixed on the inner peripheral surface of the bending piece $82_n$ provided at the outermost proximal end by, e.g., bonding or brazing. That is, as shown in FIG. 16B, the inner peripheral surface of the bending piece $82_n$ provided at the outermost proximal end is formed as fixing portions 286a and 286b at the proximal ends of the coil pipes 282a and 282b in the R direction and the L direction, whereby the coil pipes 282a and 282b are fixed.

The angle wire 234a in the R direction is inserted into one coil pipe 282a, and the angle wire 234b in the L direction is inserted into the other coil pipe 282b. It is to be noted that non-illustrated coil pipe guides are formed on the bending pieces $82_{m+1}, \ldots, 82_{n-1}$ between the intermediate bending piece $82_m$ and the bending piece $82_n$ which is provided at the outermost proximal end, whereby the angle wires 234a and 234b inserted into the coil pipes 282a and 282b and the coil pipes 282b and 282b are guided, respectively.

When the bending portion 64 is bent in, e.g., the R direction (the right direction), the bending pieces 82a, 82b, 82c, ..., $82_{m-1}$ provided on the distal end side of the intermediate bending piece $82_m$ in the bending pieces 82a, 82b, 82c, ..., $82_{m-1}, 82_m, 82_{m+1}, \ldots, 82_{n-2}, 82_{n-1}, 82_n$ of the bending tube 82 rotationally move with respect to each other. Since the coil pipes 282a and 282b add resistive force for expansion and contraction, the bending pieces $82_m, \ldots, 82_n$ provided on the proximal end side of the intermediate bending piece $82_m$ are hard to rotationally move with respect to each other by the coil pipe 282a. Therefore, when the same bending piece is used for the bending pieces 82b, 82c, ..., $82_{m-1}, 82_m, 82_{m+1}, \ldots, 82_{n-2}, 82_{n-1}$ between the bending piece 82a at the outermost distal end and the bending piece $82_n$ at the outermost proximal end, the proximal end side can be formed to be hardly bent as compared with the distal end side. Therefore, it is possible to carry out the control in such a manner that a bending angle of the bending portion 64 becomes larger on the distal end side than on the proximal end side.

When the bending portion 64 is bent in the L direction (the left direction), the same control can be carried out.

Further, as different from a hard pipe, the coil pipes 282a and 282b which are preferably, for example, closely wound deform in response to application of external force. Therefore, when the coil pipes 282a and 282b are used, these pipes are not formed as a hard portion, but they function as a part of the bendable bending portion 64.

It is to be noted that the description has been given as to the example where both the coil pipe 282a in the R direction and the coil pipe 282b in the L direction are arranged in FIG. 13, FIG. 16A, and FIG. 16B, but a configuration where the coil pipe is arranged in either the R direction or the L direction is also preferable.

[Additional Notes]

An electronic endoscope includes: an insertion portion which includes an insulative distal end hard portion main body at a distal end thereof and is inserted into a hole; an operation portion which is provided at a proximal end portion of the insertion portion and includes a connector connecting portion electrically connected to a ground portion; a ground metal member which is provided between the distal end hard portion main body of the insertion portion and the operation portion, forms a structure of the insertion portion, and is electrically conductive with respect to the ground portion through the connector connecting portion; an observation optical system which includes an optical element and a frame member which holds the optical element and has conductive properties, and is extended from the distal end of the insertion portion toward the operation portion; and a conductive connecting portion which allows the frame member of the observation optical system to become electrically conductive with respect to the ground metal member.

As described above, since the ground metal member is provided between the distal end hard portion main body of the insertion portion and the operation portion to form the structure of the insertion portion, the outer diameter of the insertion portion is hardly affected. Further, when the conductive connecting portion is electrically connected to the ground portion to become electrically conductive and the conductive connecting portion becomes electrically conductive with respect to the frame member having conductive properties in the observation optical system, the ground metal member and the frame member of the observation optical system have the same potential as the ground portion. Therefore, a high-frequency leak current or static electricity can be prevented from affecting the optical element, e.g., an imaging element in the observation optical system.

That is, in this electronic endoscope, the outer diameter of the insertion portion is narrowed as much as possible, and the static electricity or the high-frequency leak current can be prevented from affecting the observation optical system.

It is preferable that the ground metal member has a cylindrical shape, the frame member is arranged on the inner side of the cylindrical ground metal member, and the conductive connecting portion includes a contact portion with conductive properties which is formed on a part of the ground metal member and protrudes toward the frame member to abut on the frame member.

Therefore, the ground metal member as the structure has a cylindrical shape, the frame member is arranged therein, and the conductive connecting portion has the contact portion which is formed on a part of the ground metal member and protrudes toward the frame member, whereby the ground metal member and the frame member of the observation optical system can have the same potential as the ground portion by adopting the simple configuration.

It is preferable that in the conducive connecting portion, an adhesive with conductive properties is filled between the ground metal member and the frame member.

Therefore, with the simple configuration, namely, the adhesive with conducive properties, the ground metal member and the frame member of the observation optical system can have the same potential as the ground portion.

It is preferable that the conductive connecting portion allows the ground metal member and the frame member to become electrically conductive to each other through a conductive member.

Therefore, with the simple configuration that the conductive member is arranged between the conductive connecting portion and the ground metal portion, the ground metal member and the frame member of the observation optical system can have the same potential as the ground portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electronic endoscope comprising:
   an insertion portion which includes an insulative distal end hard portion main body at a distal end thereof and which is configured to be inserted into a hole;
   an operation portion which is provided at a proximal end portion of the insertion portion and which includes a connector connecting portion electrically connected to a ground portion;
   a ground metal member which is provided between the distal end hard portion main body of the insertion portion and the operation portion, which forms a structure of the insertion portion, and which is electrically conductive with respect to the ground portion through the connector connecting portion;
   an observation optical system which includes an optical element and a frame member having conductive properties and holding the optical element, and which is extended from the distal end of the insertion portion toward the operation portion; and
   a conductive connecting portion which allows the frame member of the observation optical system to become electrically conductive with respect to the ground metal member,
   wherein an adhesive with conductive properties is filled between the ground metal member and the frame member.

2. The electronic endoscope according to claim 1, wherein the ground metal member has a cylindrical shape,
   the frame member is arranged on the inner side of the cylindrical ground metal member, and
   the conductive connecting portion includes a contact portion with conductive properties which is formed on a part of the ground metal member and protrudes toward the frame member to abut on the frame member.

3. An endoscopic system comprising:
   the electronic endoscope according to claim 1; and
   an external device having the ground portion.

4. The electronic endoscope according to claim 2, wherein the contact portion has a tongue-like shape, and is configured to be folded toward the frame member arranged on the inside of the ground metal member and brought into contact with the frame member.

5. The electronic endoscope according to claim 1, wherein the frame member has a cockscomb shape configured to be closer to the ground metal member.

* * * * *